(12) United States Patent
Hindinger et al.

(10) Patent No.: US 7,693,579 B2
(45) Date of Patent: Apr. 6, 2010

(54) ELECTRONIC ACUPUNCTURE DEVICE AND SYSTEM, AND METHOD OF MANAGING MERIDIAN ENERGY BALANCE DATA OF A PATIENT

(75) Inventors: John R. Hindinger, Dearborn, MI (US); Ramon Nunez, Waterford, MI (US)

(73) Assignee: Charter IP, LLC, The Plains, VA (US)

( * ) Notice: Subject to any disclaimer, the term of this patent is extended or adjusted under 35 U.S.C. 154(b) by 945 days.

(21) Appl. No.: 11/377,881

(22) Filed: Mar. 17, 2006

(65) Prior Publication Data
US 2006/0212104 A1 Sep. 21, 2006

Related U.S. Application Data

(60) Provisional application No. 60/662,547, filed on Mar. 17, 2005, provisional application No. 60/690,890, filed on Jun. 16, 2005.

(51) Int. Cl.
*A61N 1/18* (2006.01)

(52) U.S. Cl. .......................................... 607/72; 607/46

(58) Field of Classification Search ........................ None
See application file for complete search history.

(56) References Cited

U.S. PATENT DOCUMENTS

| 4,180,079 | A | | 12/1979 | Wing |
| 5,012,816 | A | * | 5/1991 | Lederer ...................... 600/548 |
| 5,251,637 | A | | 10/1993 | Shalvi |
| 5,851,223 | A | * | 12/1998 | Liss et al. ..................... 607/46 |
| 6,119,038 | A | * | 9/2000 | Cook ............................. 607/3 |
| 6,934,581 | B2 | | 8/2005 | Kanevsky |
| 2003/0045809 | A1 | * | 3/2003 | Kanevsky ................... 600/547 |
| 2004/0087838 | A1 | | 5/2004 | Galloway et al. |
| 2004/0230256 | A1 | * | 11/2004 | Lin-Hendel .................. 607/72 |
| 2005/0015017 | A1 | | 1/2005 | Horne et al. |

* cited by examiner

*Primary Examiner*—Carl H. Layno
*Assistant Examiner*—Jon-Eric C. Morales
(74) *Attorney, Agent, or Firm*—Charter IP LLC; Matthew J. Lattig

(57) ABSTRACT

An electronic acupuncture system may include a hand-held, electronic acupuncture device in communication with a remote computing device. The electronic device may include a grip probe held by the patient for applying a first diagnosis voltage through the patient's body, and a search probe applying pressure against the skin of the patient and receiving measurable diagnosis data from the patient. The received diagnosis data is converted into a digital signal for display on the electronic acupuncture device and/or for processing and display at the remote computing device. Based on the diagnosis data, the patient may be treated with a second treatment voltage.

38 Claims, 16 Drawing Sheets

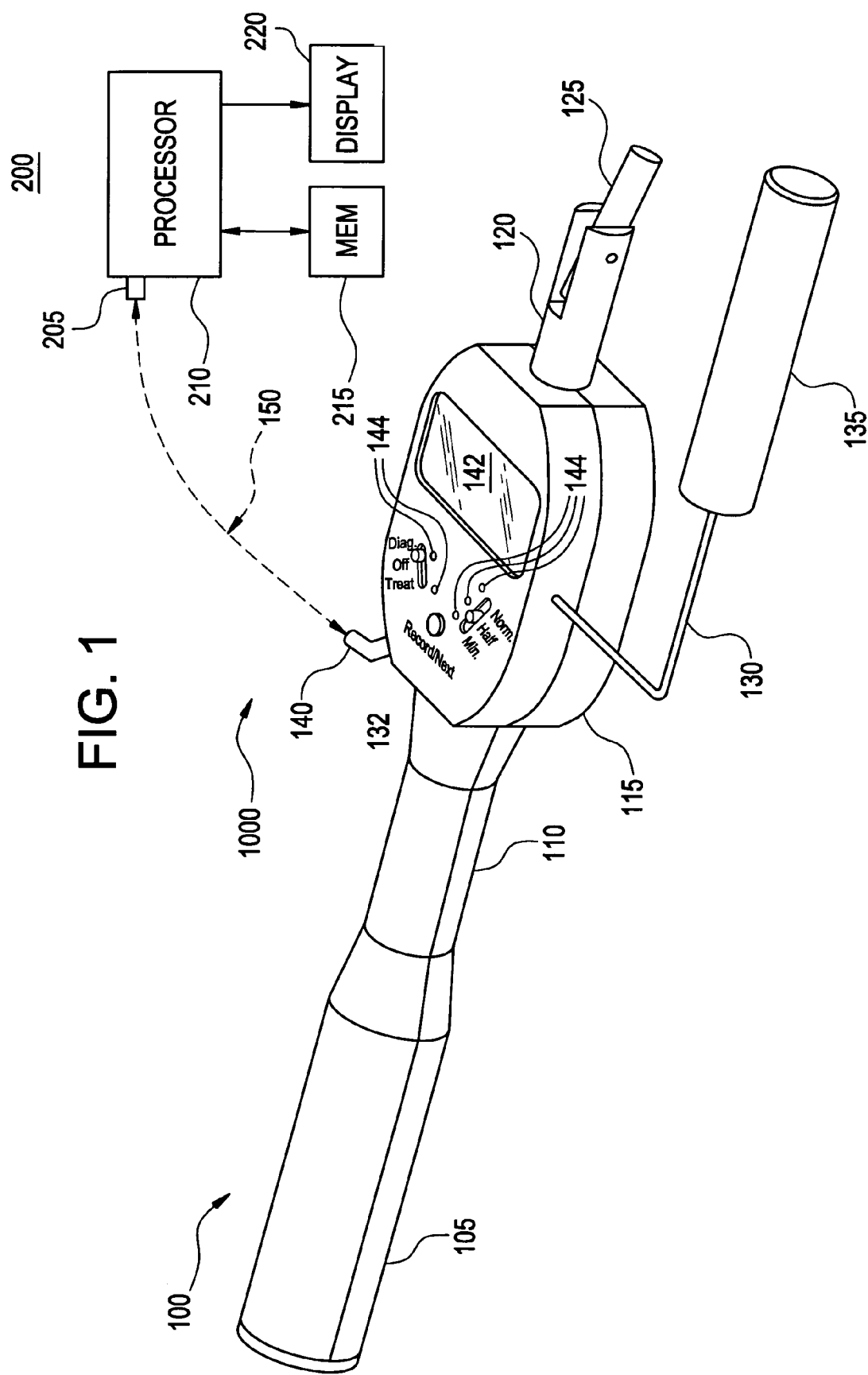

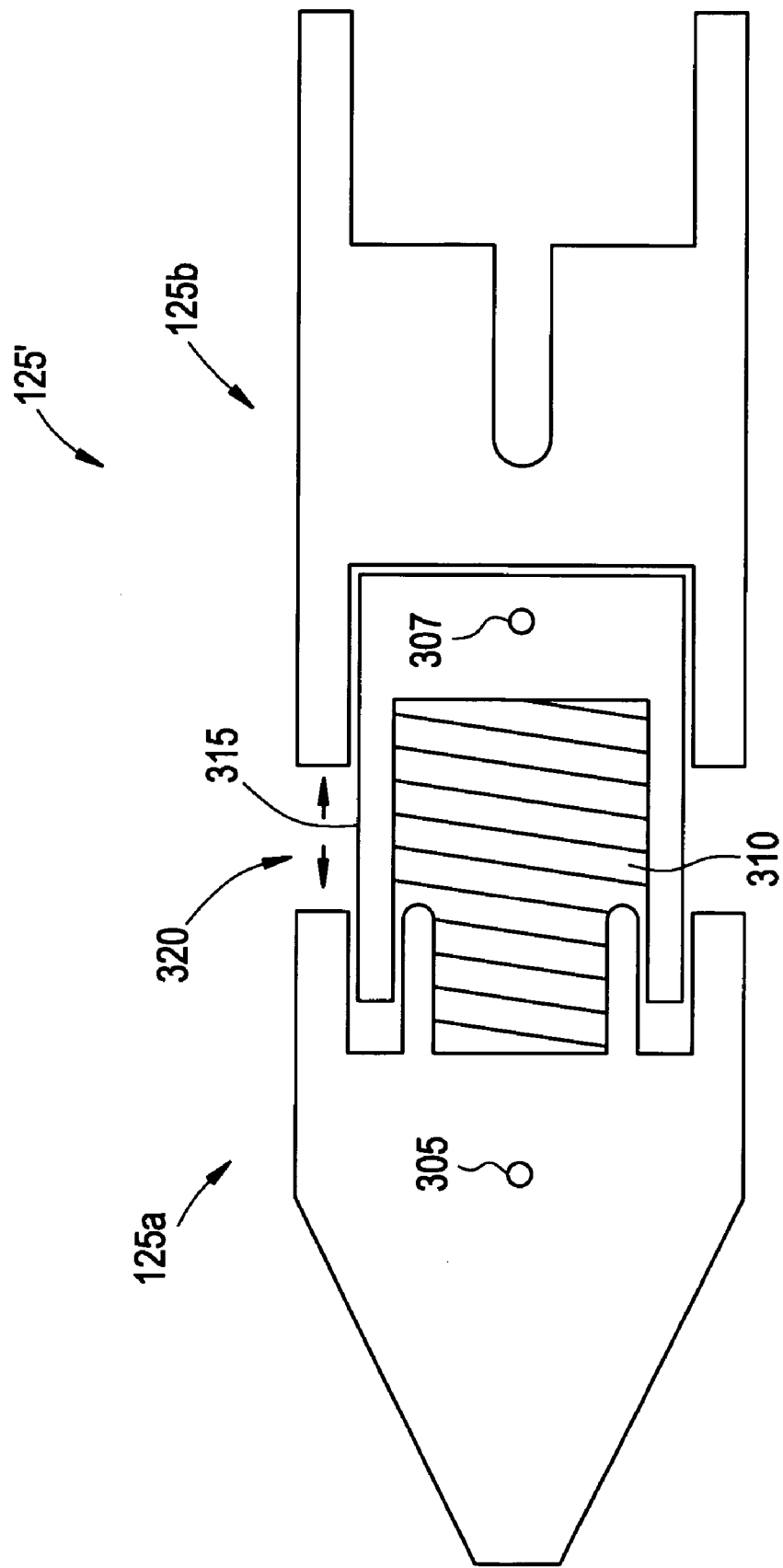

FIG. 5A

| | Lu 9 | | Pc 7 | | Ht 7 | | Li 5 | | Th 4 | | Si 5 | | Sp 3 | | Lv 3 | | Ki 6 | | Bl 65 | | G 40 | | S 43 | |
|---|---|---|---|---|---|---|---|---|---|---|---|---|---|---|---|---|---|---|---|---|---|---|---|
| NAME | L | R | L | R | L | R | L | R | L | R | L | R | L | R | L | R | L | R | L | R | L | R | L | R |
| 505 | 190–5 | 160–5 | 170–5 | | 140–5 | | 170–5 | | 200–5 | | 200–5 | | 160–5 | | 130–5 | | 160–5 | | 150–5 | | 130–5 | | 140–5 | | 160–5 |

| STIM | L 9 | P 9 | H 9 | SI 3 | Th 3 | Li 11 | Sp 2 | Lv 8 | K 7 | B 67 | G 43 | S 41 |
|---|---|---|---|---|---|---|---|---|---|---|---|---|
| SED | L 5 | P 7 | H 7 | SI 8 | Th 10 | Li 2 | Sp 5 | Lv 2 | K 1 | B 65 | G 38 | S 45 |

540

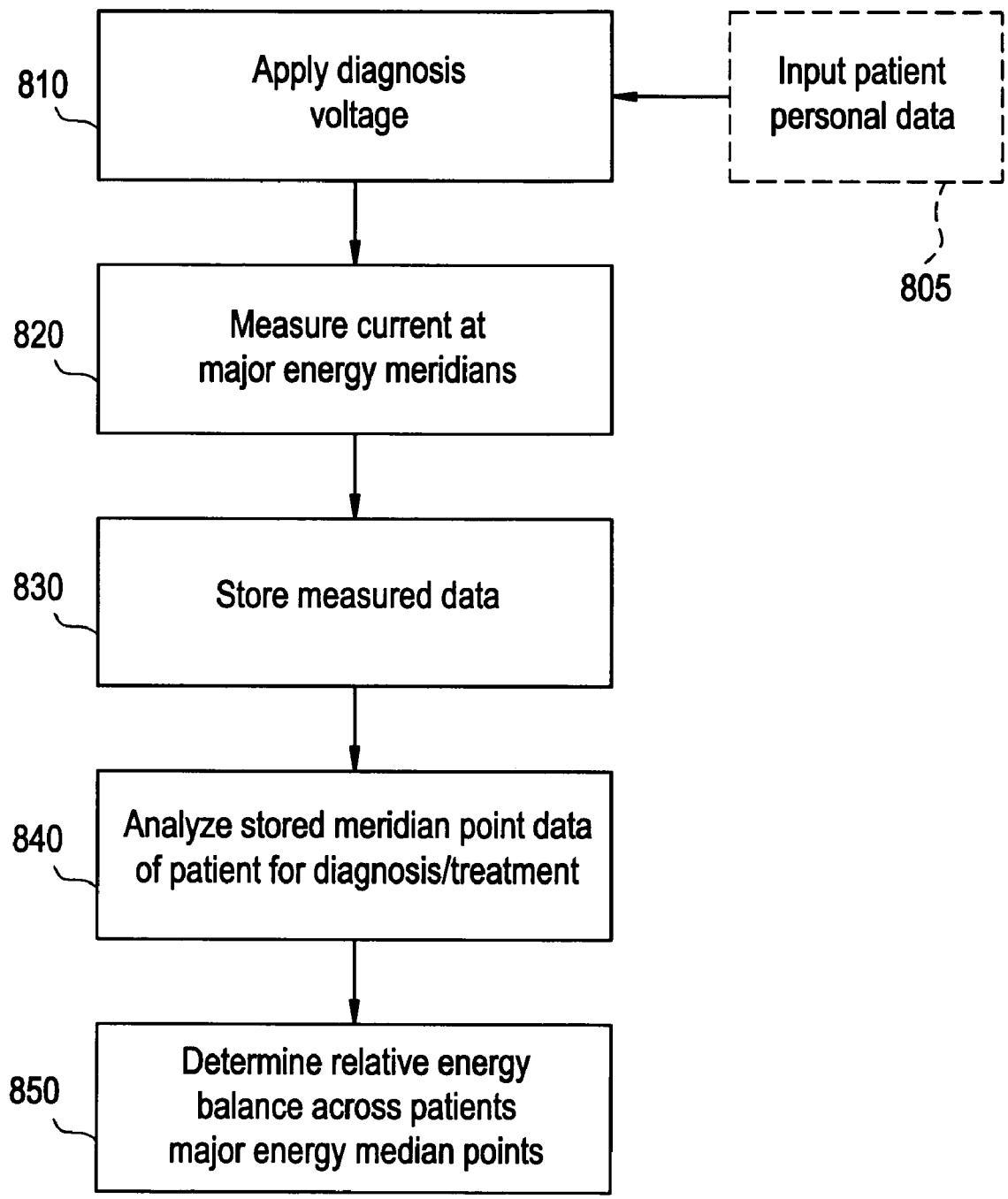

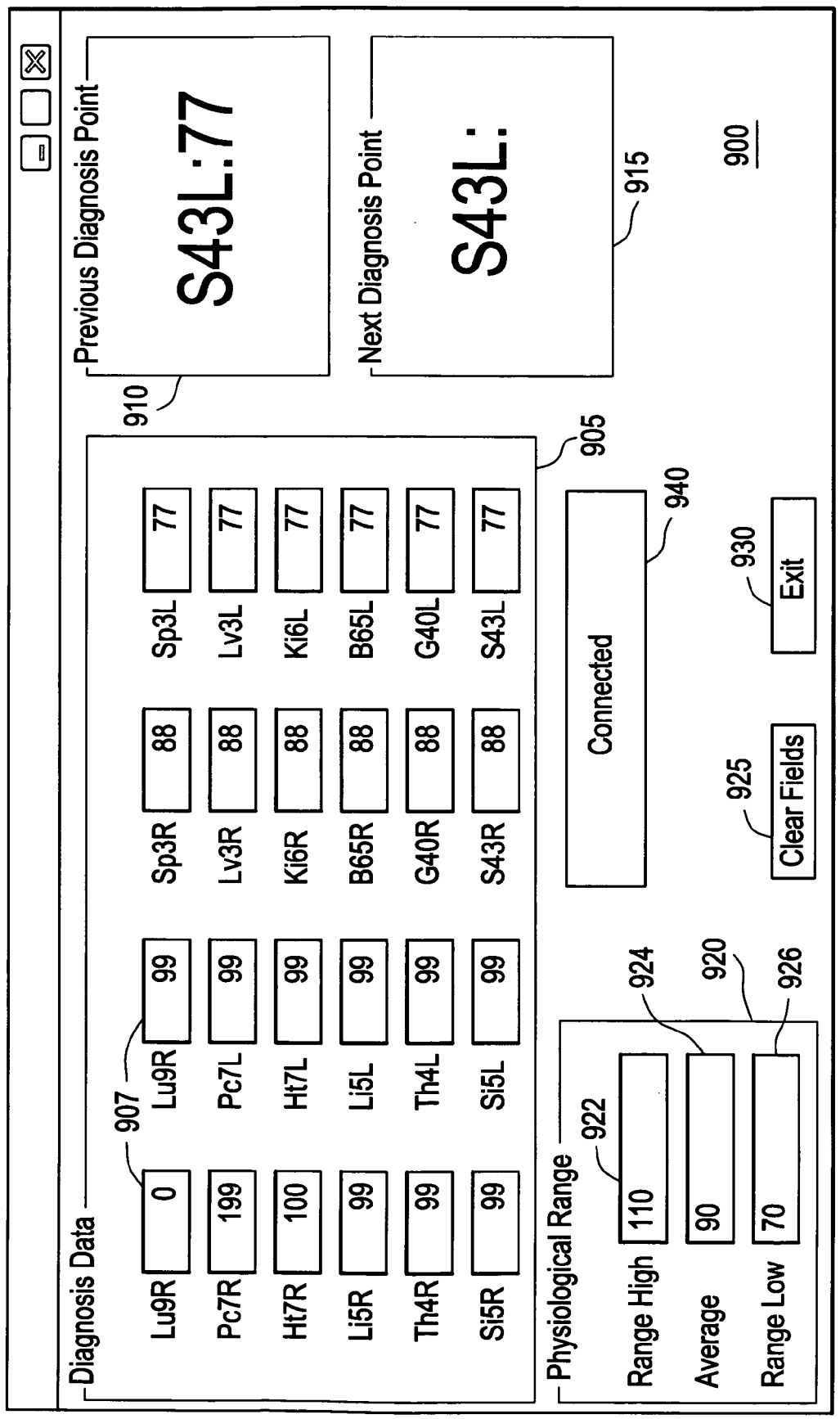

ELECTRONIC ACUPUNCTURE DEVICE AND SYSTEM, AND METHOD OF MANAGING MERIDIAN ENERGY BALANCE DATA OF A PATIENT

PRIORITY STATEMENT

This application claims the benefit under 35 U.S.C. §119 (e) to the following U.S. Provisional Patent Applications: Ser. No. 60/662,547, filed Mar. 17, 2005 to John R. Hindinger et al. and entitled "ELECTRONIC ACUPUNCTURE DEVICE AND SYSTEM"; and Ser. No. 60/690,890, filed Jun. 16, 2005 to John R. Hindinger et al. and entitled "ELECTRONIC ACUPUNCTURE DEVICE AND SYSTEM". The entire contents of each of the provisional applications are hereby incorporated by reference herein.

BACKGROUND OF THE INVENTION

1. Field of the Invention

The present invention relates generally to an electronic acupuncture device and system so as to provide noninvasive acupuncture diagnosis and treatment for a patient, and to a method of measuring, analyzing and balancing meridian energy levels of a patient so as to provide noninvasive acupuncture treatment for the patient.

2. Description of Related Art

Although few in the western hemisphere understand acupuncture, western medicine is waking up to its benefits. In general, acupuncture may be described as managing the body's life energy, or Chi, by redirecting the body's energy through a series of points on the body that form lines called meridians. Meridians map loosely to internal organs, providing another perspective from which to view acupuncture's benefits. Although theories disagree as to how the body transfers Chi across meridians, empirical evidence to its efficacy is overwhelming.

By studying thousands of years of predominantly Chinese medicine, acupuncturists know the locations of acupuncture points and how to insert needles into these points, known as energy meridian points, in order to govern Chi flow. Western medicine has verified the existence of many energy meridian points by measuring the high electrical conductivity at these points.

In the early 1950's, a Japanese doctor applied the conductivity principle in inventing the Ryodoraku protocol, a quick and simplified methodology of reaping many of acupuncture's benefits with electricity. Dr. Yoshio Nakatani noted areas of altered electrical conductivity on the skin of patients with various diseases. These areas were found to be points of approximately 1 cm diameter, generally in lines following the classical Chinese acupuncture meridians. Because these points offered increased electrical conductance, he named these points "ryodoraku" (ryo=good, do=(electro) conductive, raku=line.)

Dr. Nakatani refined his procedures to encompass both diagnosis and treatment. Diagnosis was performed with an electrical instrument measuring electrical conductivity of the skin. By measuring the conductivity of each energy meridian, energetic excesses and deficiencies could be located. Treatment consisted of stimulating specific acupuncture points to either "tonify" a deficient meridian, or "sedate" an excessive meridian. An additional set of acupuncture points was used to balance meridians that showed significant energetic differences between the right and left sides of the body. Thus, in general, a simple form of the Ryodoraku technique treats multiple conditions by balancing the body's Chi across its twelve (12) major or main energy meridians: heart, pericardium, lung, triple heater (San Jiao), large intestine, small intestine, kidney, bladder, gall bladder, spleen, stomach and liver.

Prior art electronic acupuncture units are typically bulky, involve little or no automation, and exhibit no voltage control. The prior art electronic acupuncture devices are little more than a power source having either a voltage that tapers to zero, which sacrifices diagnosis accuracy, or a voltage below those recommended by Ryodoraku, and a memory which typically stores inaccurate conductivity readings. Users typically must plot the diagnosis by hand prior to rendering any kind of treatment.

A prior art acupuncture device by Miridia Technologies known as the AcuGraph® incorporates a software package that runs on a user's personal computer (PC), and uses electronic hardware powered by and attached to the PC. However, the electronic hardware attached to the AcuGraph® is incapable of providing accurate Ryodoraku diagnosis voltages because it draws power at approximately five (5) volts from a computer's Universal Serial Bus (USB) port, but incorporates no circuitry to boost the voltage to the twelve (12) volts called for in the Ryodoraku diagnosis. Although the AcuGraph® uses an algorithm to normalize its readings as if they were taken at the correct voltage, the AcuGraph® is incapable of administering proper diagnosis voltage to the user, introducing the potential for deviation from the Ryodoraku protocol. In addition, the AcuGraph® is not designed for and cannot produce the higher voltages required for administering needle-free treatment, and thus serves only as a diagnostic tool.

Further, diagnosing the acupuncture meridians is typically difficult for many practitioners. This is because the traditional methods for doing so, such as pulse diagnosis, are complex and typically require decades to master.

SUMMARY OF THE INVENTION

An example embodiment of the present invention is directed to an electronic acupuncture system adapted to provide noninvasive acupuncture treatment for a patient. The system may include a hand-held electronic acupuncture device in communication with a remote computing device. The electronic acupuncture device may be configured to communicate measurable patient data to the remote computing device for diagnosis or treatment of the patient.

Another example embodiment of the present invention is directed to a hand-held, electronic acupuncture device. The device may include a handhold area operatively connected to an extension member which includes a main electronics unit. The main unit may include a display thereon and intelligence therein for providing one of diagnosis and/or treatment of a patient based on measurable patient data. The device may include a search probe operatively connected to the main unit, and a grip probe operatively connected via an electrical connector to the main unit.

Another example embodiment of the present invention is directed to an electronic acupuncture device comprising a main electronics unit and a search probe operatively attached thereto. The device may be configured to apply a diagnosis voltage to a patient and measure a current from the patient representing energy meridian data of the patient, and to apply a different treatment voltage to the patient based on an analysis of the energy meridian data.

Another example embodiment of the present invention is directed to a method of managing meridian energy data of a patient to treat the patient. In the method, a diagnosis voltage may be applied to the patient at each of the patient's major energy meridian points. Data corresponding to the patient's major energy meridian points may be measured based on the applied diagnosis voltage and analyzed. A relative energy balance across the patient's major energy meridian points may be determined based on the analysis.

BRIEF DESCRIPTION OF THE DRAWINGS

Example embodiments of the present invention will become more fully understood from the detailed description given herein below and the accompanying drawings, wherein like elements are represented by like reference numerals, which are given by way of illustration only and thus are not limitative of the example embodiments of the present invention.

FIG. 1 is an illustration of a hand-held electronic acupuncture device and system in accordance with an example embodiment of the present invention.

FIG. 3 is another example of a search in accordance with an example embodiment of the present invention.

FIGS. 5A and 5B illustrate an example Ryodoraku chart of a patient's Stimulation (STIM or excitation) and Sedation (SED or inhibition) points in accordance with an example embodiment of the present invention.

FIGS. 7B-1 and 7B-2 illustrate a circuit diagram of an electronic circuit included in a hand-held electronic acupuncture device in accordance with another example embodiment of the present invention.

FIG. 8 is a flow diagram for describing a method of managing meridian energy data of a patient to treat the patient, in accordance with an example embodiment of the present invention.

FIGS. 9A and 9B are screen shots illustrating exemplary data displayed to a user of the system 1000 in accordance with an example embodiment of the present invention.

DETAILED DESCRIPTION OF THE EXAMPLE EMBODIMENTS

A device that can diagnose acupuncture meridians may be a valuable medical device. Example embodiments of the present invention describe features that may accelerate, simplify and/or improve the accuracy of diagnosis as compared to prior art devices. Moreover, and as to be explained in further detail hereafter, the example embodiments of the present invention may enable a user with no prior acupuncture or meridian treatment skills to perform meridian treatment according to the Ryodoraku protocol.

Figure 7A:
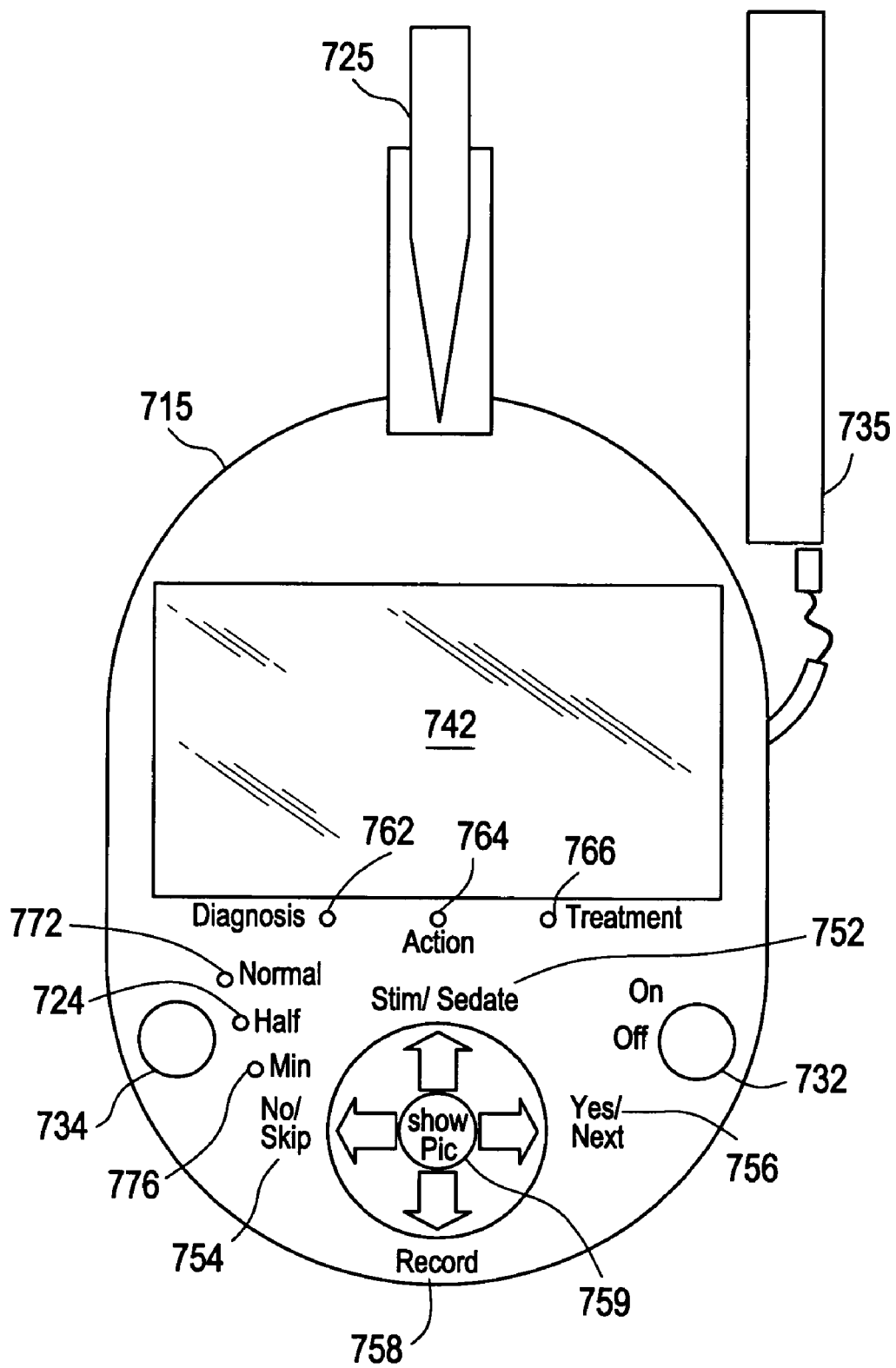
FIG. 7A illustrates an enlarged view of a main unit assembly of a hand-held electronic acupuncture device in accordance with another example embodiment of the present invention.
Figures 1, 7B:
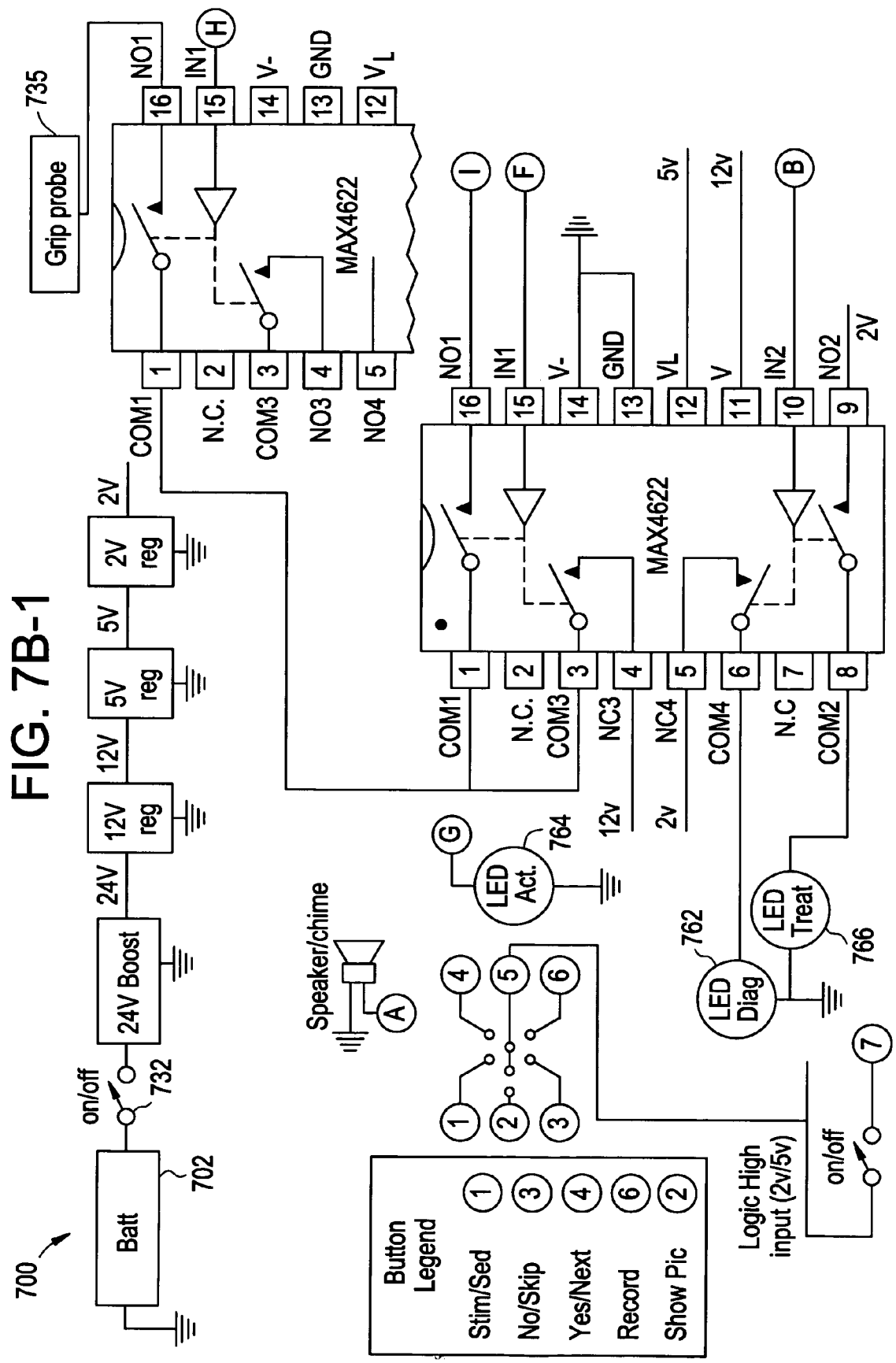
Figures 2, 7B:
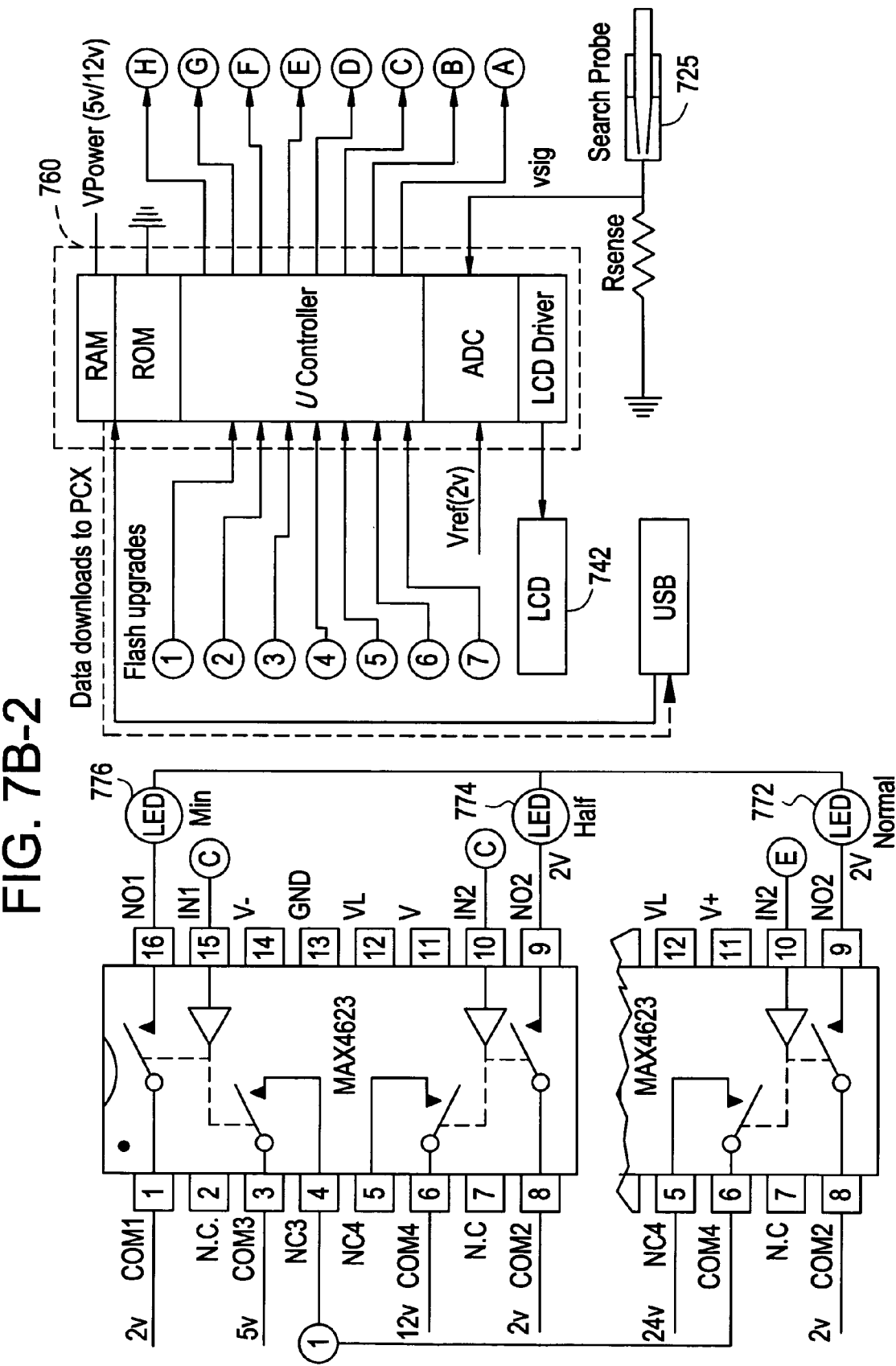

FIG. 1 is an illustration of a hand-held, electronic acupuncture device and system in accordance with an example embodiment of the present invention. Referring to FIG. 1, system 1000 may include an electronic acupuncture device 100 in operative communication with a remote computing device 200 via a wireless link 150 and a suitable user interface, for example. The remote computing device 200 may be embodied as a personal computer, work station or Personal Data Assistant (PDA) and/or integrated PDA/cell phone such as a Blackberry®, Treo® or Palm Pilot®, for example, it being understood that these are just a few of the exemplary intelligent devices which may be configurable as remote computing device 200.

The electronic acupuncture device (electronic device 100) may include a power source compartment 105 as part of a handle 110 that is operatively connected to a main unit assembly 115. The power source may be embodied as a plurality of alkaline batteries or a plurality of rechargeable cells having any of nickel metal hydride (NiMH), nickel cadmium (NiCd) or lithium-ion (Li-ion) cell chemistry. The power source may also be embodied as a self-contained rechargeable battery pack, either in a standard size or customized for the electronic acupuncture device, and the device may be operable from a standard AC wall socket outlet or from a computing device, such as drawing power from its USB port via an adapter fx=, for example. An extension 120 extends from the main unit assembly 115 and houses a search probe 125. An electrical connector 130 may electrically connect a grip probe 135 to the main unit assembly 115 of the electronic device 100.

In general, the patient grips the grip probe 135 in their hand. A caregiver, who in an example may be the patient, grasps the handle 110 of the electronic device 100 such that the search probe 125 is pressed against the patient's skin. The caregiver may actuate a suitable switch 132 on the main unit assembly 115 to energize the electronic device 100 at a desired diagnosis voltage or desired treatment voltage, for example.

As will be described in further detail below, once activated, battery cells (not shown) within the power source compartment 105 of the electronic device 100 produce an output voltage through connector 130 and grip probe 135 into the patient's body, so as to generate a current (i.e., a 'diagnosis' current or a 'treatment' current, depending on the applied voltage) through the patient. The current travels through the patient's body, is received at the search probe 125 and flows into an electronic circuit (not shown) within device 100. The measured current may be read as a conductance value, for example. on a suitable display 142 of the electronic device 100, and/or may be communicated via an antenna of a transceiver (shown generally at 140) over a suitable air link 150 such as an RF link, to be received at the remote computing device 200.

In an example, display 142 may be embodied as a liquid crystal display (LCD) panel with color or an LCD with a black and white display. However, display 142 is not limited to an LCD, and alternatively may be embodied as a plasma display panel (PDP), a cathode-ray tube (CRT) display, an organic light emitting diode (OLED) display or any other known equivalent display device, for example.

In general, electronic device 100 may be integrated through a USB protocol, wireless or hard-wired protocol or other communication or data protocols, and/or with a software interface and/or data management system running on the remote computing device 200. The USB protocol is based on an external bus standard that supports data transfer rates of 12 Mbps. A single USB port can be used to connect up to 127 peripheral devices such as mice, modems and keyboards. USB also supports Plug-and-Play installation and hot plugging.

As discussed above, communication schemes between electronic device 100 and computing device 200 may be facilitated through USB ports, either hardwired or wireless, through another hard-wired protocol such as RS-232 or another wireless protocol such as Bluetooth, and/or through voice commands from a user. Other alternative example wireless communication protocols may be based on one or more of CDMA (IS95, cdma2000 and various technology variations), UMTS (releases 99, R4, R5, R6 and above), GSM, 802.11 and/or related spread-spectrum based wireless technologies.

Various modifications will be apparent to those skilled in the art for application to communication systems or networks accessible by system 1000 based on technologies other than the above, which may be in various stages of development and intended for future replacement of or use in conjunction with the above communication networks or systems.

As shown in FIG. 1, the remote computing device 200 may include corresponding transceiver circuitry (shown generally at 205) for receiving the data and processing the patient current data therein in a suitable processor 210 such as any of the Pentium® line of microprocessors by Intel®, for example. An example transceiver 140/205 may be a Model TR105 miniature wireless transceiver by OTEK™ Corp., or similar embedded transceiver. In an example, processor 210 may be operatively connected to a memory 215 and to a display 220.

Accordingly, measurable data (such as the patient's current or conductance values reflective of the current) may be packetized in the transceiver 140 and transmitted as part of one or more packets of data wirelessly over air link 150 to an antenna at transceiver 205 operatively connected to the remote computing device 200. Alternatively, the measurable data may be transmitted over hard-wired protocols. The received data may be down-converted and demodulated as is known, and forwarded to downstream processing circuitry within processor 210.

The electronic device 100 and associated electronic circuitry therein may be powered from a suitable power source within compartment 105 such as a plurality of alkaline batteries, i.e., 4 "AA" size batteries, or by a plurality of rechargeable, removable battery cells or a rechargeable battery pack having one or more cells. Rechargeable secondary batteries for powering portable electronic devices are well known, evidenced by the battery packs used to power low-voltage devices such as cell phones, personal digital assistants (PDAs) and/or laptop computers. Accordingly, suitable power supplies may be battery packs consisting of one or more cells or batteries having any of a nickel metal hydride (NiMH), nickel cadmium (NiCd) and/or Li-ion cell chemistry with associated electrolyte. The cells may have either a cylindrical or prismatic construction depending on the shape and/or width of the power source compartment 105 and handle 110, for example.

A power source of NiMH, NiCD or Li-ion batteries or cells may be rechargeable via a battery charger. The battery charger typically includes a recharging stand or cradle to provide an AC source of charging current. The AC source may be provided from one of a wall outlet (i.e., via a plug) or from a computing device.

An example charger may be a charger having on-board electronics or intelligence, such as the MH-C2000™ universal battery charger by MAHA Energy Corp.™ for example, although chargers which do not support multiple chemistries are also applicable. The MH-C2000™ is capable of charging a wide selection of battery packs, such as four AA or AAA NiMH and NiCD battery cells at a time. An example charger such as the MH-C2000® may include built-in support for Li-ion, NiMH and NiCD rechargeable battery pack chemistries, and may be configured to automatically detect battery pack type and battery voltage. An embedded microprocessor may be included therein to constantly monitor the charging process in an effort to prolong battery life, and/or for communication with external electronic devices.

The electronic device 100 may be configured to have battery pack terminals (e.g., rail-style or tower-style terminal configuration, as is known in the art) within compartment 105, which may be exposed at an end thereof for matingly engaging charger terminals in the cradle or stand of the battery charger. In additional to power terminals, an example battery pack within device 100 may have sense and /or communication terminals for communication with corresponding terminals in the charger. Accordingly, the battery charger in one example may be configured to upload data stored in the electronic device via communication terminals to the charger, for transmission or communication to an external computing device such as remote computing device 200, for example.

In an example, the remote computing device 200 may be embodied in hardware and/or software to include a digital microprocessor within a suitable personal computer that includes a wireless hub and associated transceiver components and circuitry. However, instead of a digital microprocessor, an analog processor, digital signal processor, one or more programmable integrated circuits, and/or one or more application specific integrated circuits (ASICs) controlled by a suitable microcontroller or microprocessor may be used in lieu of a digital microprocessor in the remote computing device 200. Power to the remote computing device 200 may be provided by a suitable AC power (line) source or by a rechargeable battery pack as described above.

As shown in FIG. 1, the electronic device 100 includes a plurality of LEDs which in general are indicative of given voltages applied within device 100 so as to generate the desired voltage to the patient. As will be described in further detail below, a dedicated LED may represent generation of a diagnosis voltage within the electronic circuit therein and another dedicated LED may represent a treatment voltage being generated by the electronic circuit of device 100. Selection of a diagnosis or treatment voltage to be output by the power source through the patient via grip probe 135 may be effectuated via user manipulation of given switches 132, 134, which in an example may be double-position, double-throw (DPDT) switches.

Figure 2:
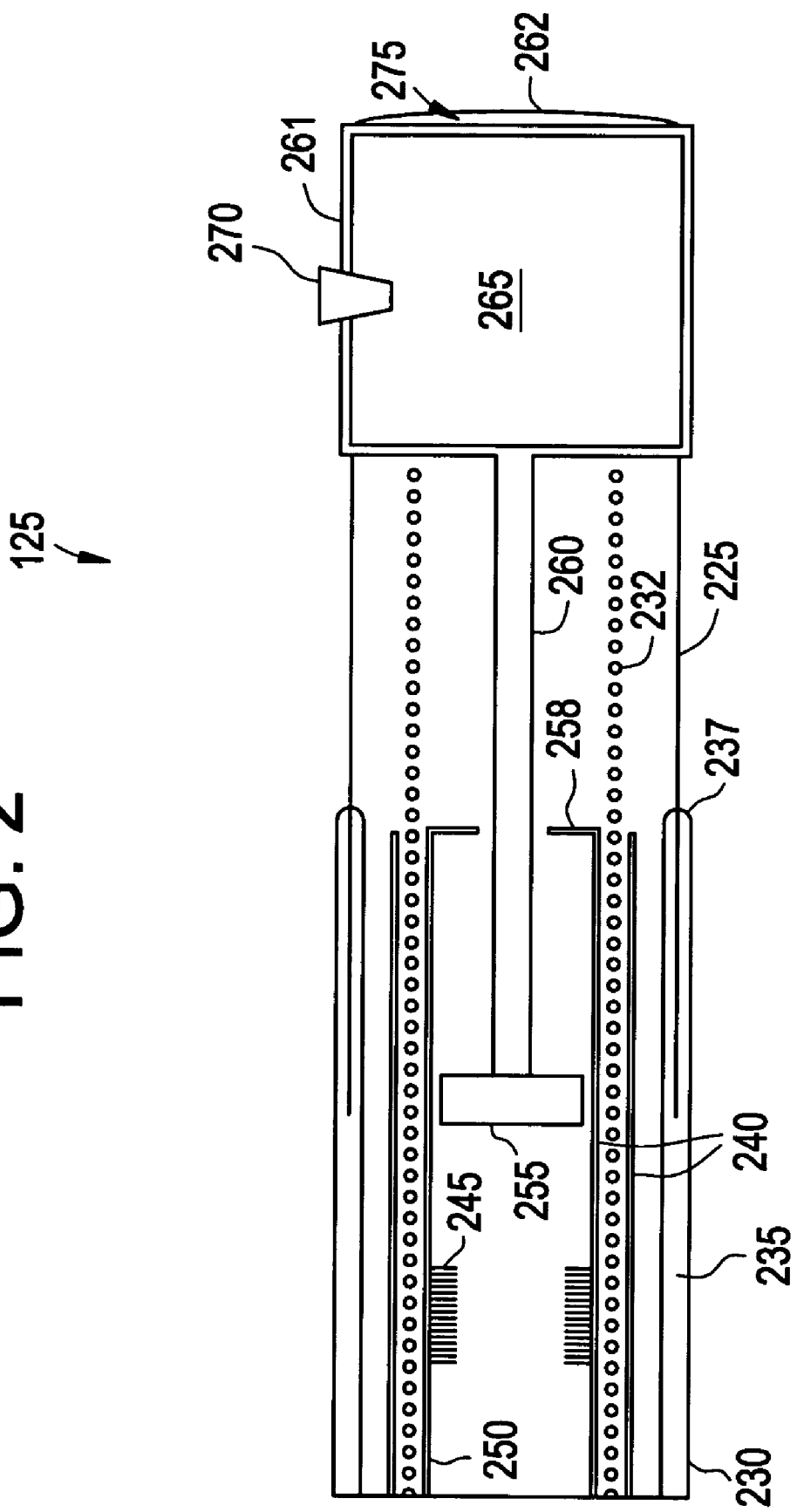
FIG. 2 is a drawing of an example search probe for the acupuncture device in accordance with an example embodiment of the present invention.

FIG. 2 is a detailed illustration of the search probe 125 of the acupuncture device in accordance with an example embodiment of the present invention. Referring to FIG. 2, the search probe 125 may include a plastic cylinder 230 as an outer shell, which may provide mechanical support for a hammer head 261 of the search probe 125. The plastic cylinder 230 may be of a suitable thickness and may be molded into a metal base, for example.

The search probe 125 may include a plurality of inner cylinders 240 which may be formed of a suitable plastic material. Cylinders 240 may be connected to a metal hammer base 250. A spring 232 may connect the hammer base 250 with a hammer head tip 262. A groove 235 in the plastic cylinder 230 may allow for motion of a moving cylinder 225. A tip 237 of the plastic cylinder 230 may be a ring that provides a mechanical boundary of the hammer head tip 262 longitudinal motion. As shown in FIG. 2, the moving cylinder 225 may provide mechanical support to the hammer head tip 262 and slide within the cylinder 230 along the longitudinal axis of cylinder 230.

As shown in FIG. 2, for electrical connection a metal brush ring 245 may be provided, in which the electrical connection between the brush ring 245 and the hammer base 250 is sealed within a suitable plastic. A metal plunger head 255 is configured to make electrical connection with the brush ring 245 and may also act to restrict the hammer head tip 262 from being ejected.

A plastic annulus 258 may permit plunger rod 260 motion and provides the mechanical boundary for the plunger head 255 longitudinal motion, as shown in FIG. 2. Plastic annulus 258 also provides a boundary for a fluid such as oil for dampening the motion of plunger head 255. Plunger rod 260 may be a conducting metal and may provide mechanical support, providing electrical connectivity with the plunger head 255.

The hammer head 261 may be composed of a conducting metal, but may also have a hollow interior with a reservoir 265 configured to hold a suitable fluid to facilitate transfer of current from the patient into an electronic circuit of the electronic device 100. Accordingly, the search probe 125 may exhibit a self-wetting feature. As shown in FIG. 2, a screw 270 may be removed and/or inserted so as to allow (or prevent) fluid flow into or out of the reservoir 265. The hammer head 261 may include a semi-permeable material 275 or other material with substantially small or microscopic holes serving as a fluid filter at tip 262. This may permit constant moisture at the tip 262, for example. The source of the constant moisture may be the fluid constrained within reservoir 265, for example, or it may include a suitable pipe or flexible hose connection to a larger reservoir located elsewhere on the electronic acupuncture device 100 (not pictured).

In an example, the interface where the search probe 125 is attached to the main unit 115 may be waterproofed. In another example, the search probe 125 may be rotatable and may be adapted so as to lock in place in a particular position or orientation. In a further example, the search probe 125 may include a pressure sensitivity mechanism for tip 262 (not shown).

In another aspect, tip 262 could be provided with an insulating cover (not shown) to limit current during treatment. For example, a number of different covers could be provided to attenuate or lower current felt by the patient, depending on the patient's comfort. Although not shown in FIGS. 1 and 2, electronic device 100 could be provided with alligator clips to provide voltages that generate currents through the patient for a potential needling acupuncture application.

FIG. 3 is another example of a search in accordance with an example embodiment of the present invention. FIG. 3 shows a cut-away side view of a search probe 125'. In FIG. 3, search probe 125' has a two piece construction, a distal probe end 125a and a proximal end 125b that is connectable to extension 120 (not shown) via rotation point 307 be suitable fastening means such as a pin, screw, etc. The distal probe end 125a is attachable to the proximal end 125b at rotation point 305 via suitable fastening means.

The probe 125' provides pressure control by use of a spring 310 within a non-conductive cylinder 315 that is situated between the distal and proximate ends 125a, 125b. A counter spring force is exerted against the direction of pressure of the probe tip 362 against the patient. This causes the spring to compress, narrowing gap 320 between ends 125a, 125b. The caregiver or patient has an indication of a proper pressure once the metal surfaces of the ends 125a, 125b engage or touch, such that an electrical path is established and a proper current measurement can be made. Accordingly, the arrangement in FIG. 3 may permit current to flow when a minimum pressure is applied, which, while not preventing the user from applying too much pressure, may help the user apply an accurate pressure.

Figure 4A:
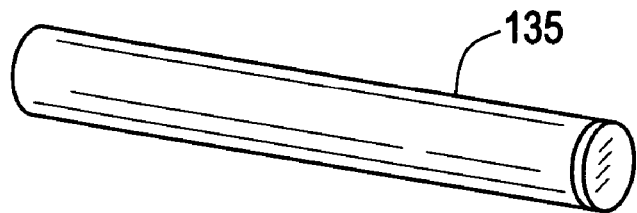
FIGS. 4A-4C illustrate example grip probe configurations for the electronic acupuncture device in accordance with an example embodiment of the present invention.
Figure 4B:
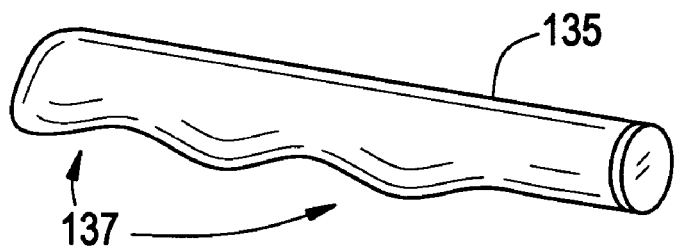
Figure 4C:
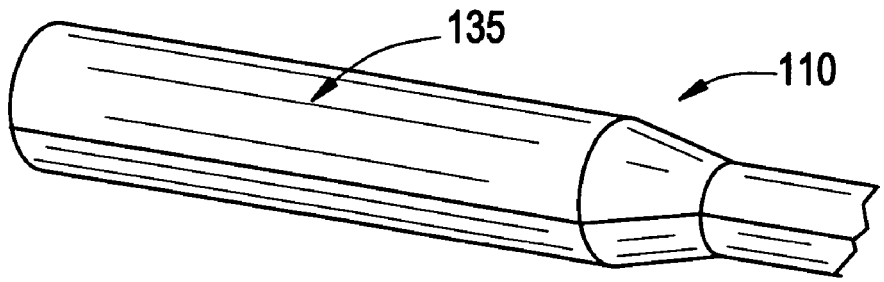

FIGS. 4A-4C are diagrams of example grip probe configurations for the electronic acupuncture device 100 in accordance with an example embodiment of the present invention.

FIG. 4A illustrates an example grip probe 135, which may be embodied as a generally cylindrically-shaped object. Grip probe 135 may be substantially hollow to reduce weight. Grip probe 135 may be composed of a suitable conductive metal or non-metal material. Example conductive metals for grip probe 135 may include but are not limited to copper, silver, brasses, leaded brasses, bronzes, copper-nickel alloys, nickel slivers, special bronzes, and alloys of one or more of these metals, and conductive plastic compounds, for example. Although not shown in the figures, a moist or water-permeable and removable slip cover may be placed over grip probe 135 to wet the patient's hand and further promote electrical conduction of current through the patient's body. Alternatively, the patient may periodically wet their hand.

Referring to FIG. 4B, in another variant the grip probe 135 may include finger grooves or indentations 137 for improved grip. The grip probe 135 in FIGS. 4A or 4B may in one example have a variable width means (not shown) to set the grip probe width as desired to facilitate grasping by the patient. Accordingly, grooved finger-grip surfaces or indentations 137 as shown in FIG. 4B may facilitate grasping of the grip probe 135 by the hand of the patient.

In FIG. 1 a search probe 125 and a grip probe 135 are used by the patient/caregiver to complete a circuit through the patient. However, the example embodiments herein envision an alternative arrangement for single person use (e.g., the caregiver is the patient). Referring to FIG. 4C, in this alternative construction the grip probe 135 (e.g., ground electrode) may be merged into the main unit handle 110 area to allow one-handed operations. Thus, the ground electrode would become part of handle 110 that is operatively connected to a main unit assembly 115. This would eliminate the need for an electrical connector 130 to electrically connect a grip probe 135 to the main unit assembly 115 of the electronic device 100. The handle 110 would thus serve two-purposes: structural support and providing a ground to complete an electric circuit for one-handed operation.

Alternatively, in another example embodiment of an electronic device having onboard intelligence to be described hereafter, the intelligent device may be adapted for use with gloves, socks, and/or straps, adhesive or other means of securing fibers containing electronic conductors to the patient's skin. This may provide for automated application of the diagnosis voltages to the diagnosis points and automated measurement of the diagnosis currents generated in the patient (not pictured).

Figure 5B:
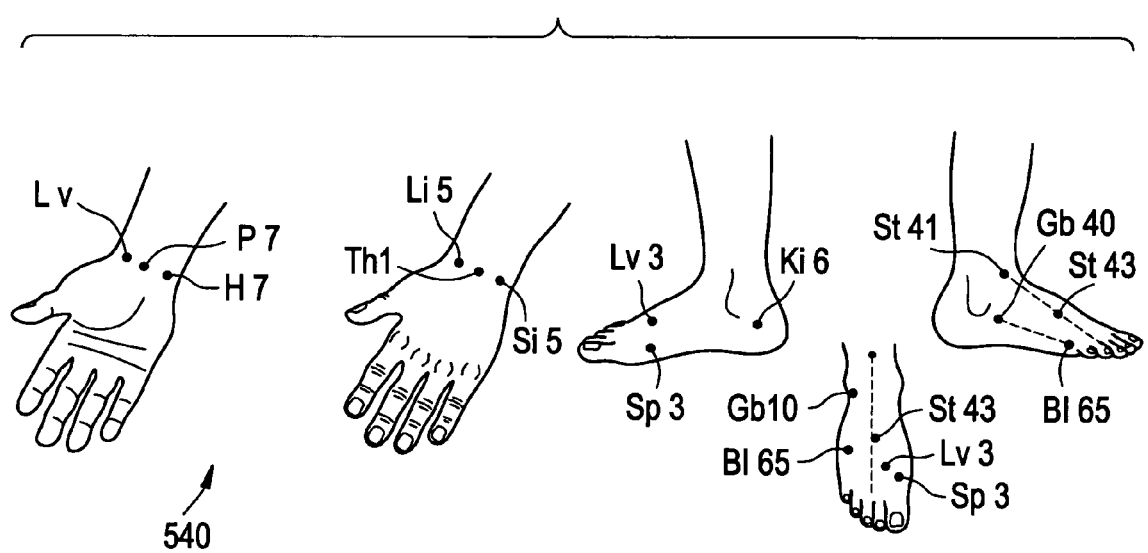

FIGS. 5A and 5B illustrate an example Ryodoraku chart 500 of a patient's Stimulation (STIM) and Sedation (SED) points in accordance with an example embodiment of the present invention. As discussed above, software at the remote computing device 200 may implement a desired protocol for graphically displaying a plurality of data points corresponding to the received current measurement from the patient. An example protocol is the Ryodoraku protocol, although the example embodiments may utilize protocols of other acupuncture and/or meridian-type analyses. For a more detailed discussion of the Ryodoraku protocol, reference may be made to the text by Nakatani et al. entitled "Ryodoraku Acupuncture", Ryodoraku Research Institute, Ltd., Tokyo, Japan, published Jul. 9, 1977. The relevant portions of the Nakatani et al. text which describe the Ryodoraku protocol are hereby incorporated in their entirety herein by reference.

The example embodiments of the present invention digitally transcribe, to software algorithms, the complex diagnosis graph created by Nakatani et al. in order to enable diagnosis calculations accurate to the Ryodoraku protocol. The visual representation of the diagnosis data may be simplified and/or normalized to a bar chart, for example, to facilitate understanding of the displayed data. The diagnosis data may be displayed on such a chart in real time as diagnosis measurements are taken. In another example, Nakatani et al.'s 'Hand 1 (H1), Hand 2 . . . Foot 1, Foot 2 . . . Foot 6' shorthand notation may be replaced with displayed notations such as 'Lung 9 (Lu9)' that are more descriptive of the points being measured on each meridian. This may simplify choices of recommended treatment points to sedate or excite certain meridians by recommending the most potent treatment point, instead of recommending multiple treatment points as described in the Nakatani et al. text.

As shown in FIG. 5A, the example Ryodoraku chart 500 shows a plot of patient current (conductance values) in each of twelve (12) interior columns. The left most and right most columns 505, 510 of the chart 500 are for plotting average current for the patient. A current point (represented as a conductance value) is plotted on the right and left sides of each of the interior 12 columns, corresponding to right and left sides of the patient's body, for a total of 24 points.

As shown on the lower portion of the chart in FIG. 5A, the STIM rows 520 are points used to stimulate the patient and the SED rows 530 are points used to sedate the patient. STIM and SED points represent part of the treatment portion of the patient using the electronic acupuncture device 100. Graphical representations (540) of the approximate locations of the 12 major energy meridian points on the hands and feet of a human being are illustrated at the bottom of chart 500, as shown in FIG. 5B. This may be used by the caregiver or patient for reference.

In an example, the electronic acupuncture device 100 is configured so as to provide a simpler mechanical system to apply the desired or optimal pressure to a patient's skin. The use of a brush ring and hammer base subassembly as shown in FIG. 2, for example, provides a more efficient, simpler and less expensive mechanical solution for applying the desired pressure in order to generate more accurate current data for the Ryodoraku protocol evaluation at the remote computing device 200. The arrangement in FIG. 2 permits current to flow through the search probe 125 only when pressure applied to the patient's skin is within a given range, as determined by the compression of a spring 232. Alternatively, the arrangement in FIG. 3 may permit current to flow when a minimum pressure is applied, which, while not preventing the user from applying too much pressure, may help the user apply an appropriate pressure to get a more accurate reading.

The example system may thus provide a noninvasive acupuncture treatment in which a hand-held electronic acupuncture device 100 is powered by a self-contained power source and includes an ammeter, i.e., a "smart probe". Accordingly, device 100 is flexible and may better serve a patient's and/or caregiver's needs. The search probe 125 may be rotatable and/or may include swiveling features which provides ease of use. In FIG. 2, the search probe 125 includes a self-moistening tip 262 to ensure proper electrical conduction of the patient's internal body current into the electronic device 100. This may provide a truer and more accurate indication of measured patient current, and may more accurately indicate the flow of stimulating or sedating current in the patient in a manner readable by the patient or caregiver, either on a suitable display 142 of the electronic device 100 or on a display 220 of the remote computing device 200.

Wireless connectivity between the electronic acupuncture device 100 and the remote computing device 200 may thus provide a system 1000 that is highly flexible, and which can provide data that may be read remotely in the patient's room within a hospital, and/or at other locations around the world, for proper diagnosis and follow-on treatment. Operation and navigation through the software on the remote computing device 200 may be designed to be accomplished wirelessly through the electronic acupuncture device 100, so that the user can render diagnosis, store and view patients' present and historical diagnosis data, and render treatment with the aid of software by using one button, such as a 'record/next' button on the device 100. Thus, the user does not have to use the remote computing device 200's controls.

In another aspect, the Ryodoraku protocol may be implemented by software executed at the remote computing device 200 so as to properly diagnose the patient by running and measuring the low-level current at 12V DC through 24 points around the wrist and/or feet. The applied diagnosis voltage may produce a current ('diagnosis current') through the patient in the 0 to 200 µA range, and the 24 points may be measured utilizing the graphical Ryodoraku protocol. As shown in FIG. 5A, the data may serve as inputs to a normalized graph 500 to compare the 24 points and produce a recommendation for stimulating or sedating the patient's energy meridians. Thereafter, the caregiver may stimulate points on the patient's body corresponding to the graph's recommendations. If desired, one or more post-treatment readings may be taken to verify that the energy meridians are balanced. Moreover, the graphical representation illustrated in FIG. 5 may be implemented in software for display and analysis on one of display 142/220.

Figure 6A:
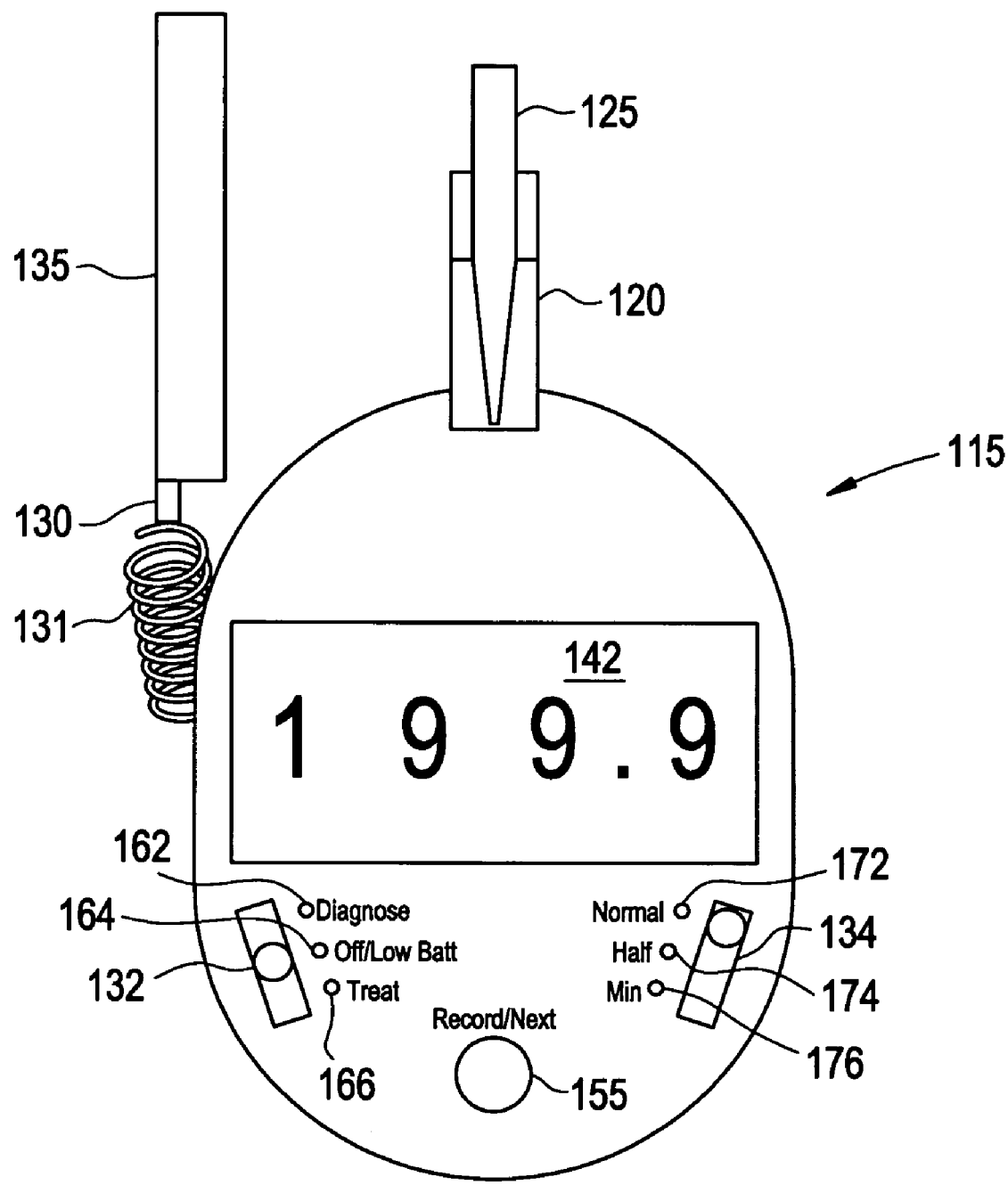
FIG. 6A illustrates an enlarged view of a main unit assembly 115 of the hand-held electronic acupuncture device 100 in accordance with an example embodiment of the present invention.

FIG. 6A illustrates an enlarged view of the main unit assembly 115 of the hand-held electronic acupuncture device 100 in accordance with an example embodiment of the present invention. In FIG. 6A, only the main unit 115, search probe 125 and grip probe 135 of the electronic device 100 are shown for purposes of clarity.

The main unit 115 includes a user-manipulated on/off switch 132 such as a DPDT switch that is movable between off, treatment and diagnose as indicated by LEDs 162, 164 and 166 on the main unit 115. Additionally switch 134 may be provided to vary or change the amount of treatment voltage applied between a normal (24 volts), half (12 volts) and minimum (5 or 6 volts) voltage level, so as to provide a variable treatment voltage to the patient. These voltage levels may be indicated on the main unit 115 by corresponding LEDs 172, 174 and 176. Other example voltage levels may include voltages above 6 volts or the ability for a user to select diagnosis and/or treatment voltages of their choosing over a range of about 5 to 30 volts, for example.

In this example, the main unit 115 does not include onboard intelligence such as an embedded microprocessor, but rather communicates data to the remote computing device 200 via suitable communication means. As shown in FIG. 6A, the grip probe 135 may be attached to the main unit 115 via a connector 130. The connector 130 may be part of an expandable spring 131 which allows the patient to grasp the grip probe 135 and pull it away from the main unit 115 for diagnosis and/or treatment. As shown in FIG. 6A, the LEDs for treatment and normal voltage (24V) are illuminated, to show that a normal 24 volt treatment voltage is being applied to the patient. Additionally, main unit 115 may include a record button 155 which enables the patient or caregiver to record measurable data, which may be communicated to the remote communicating device 200.

Figure 6B:
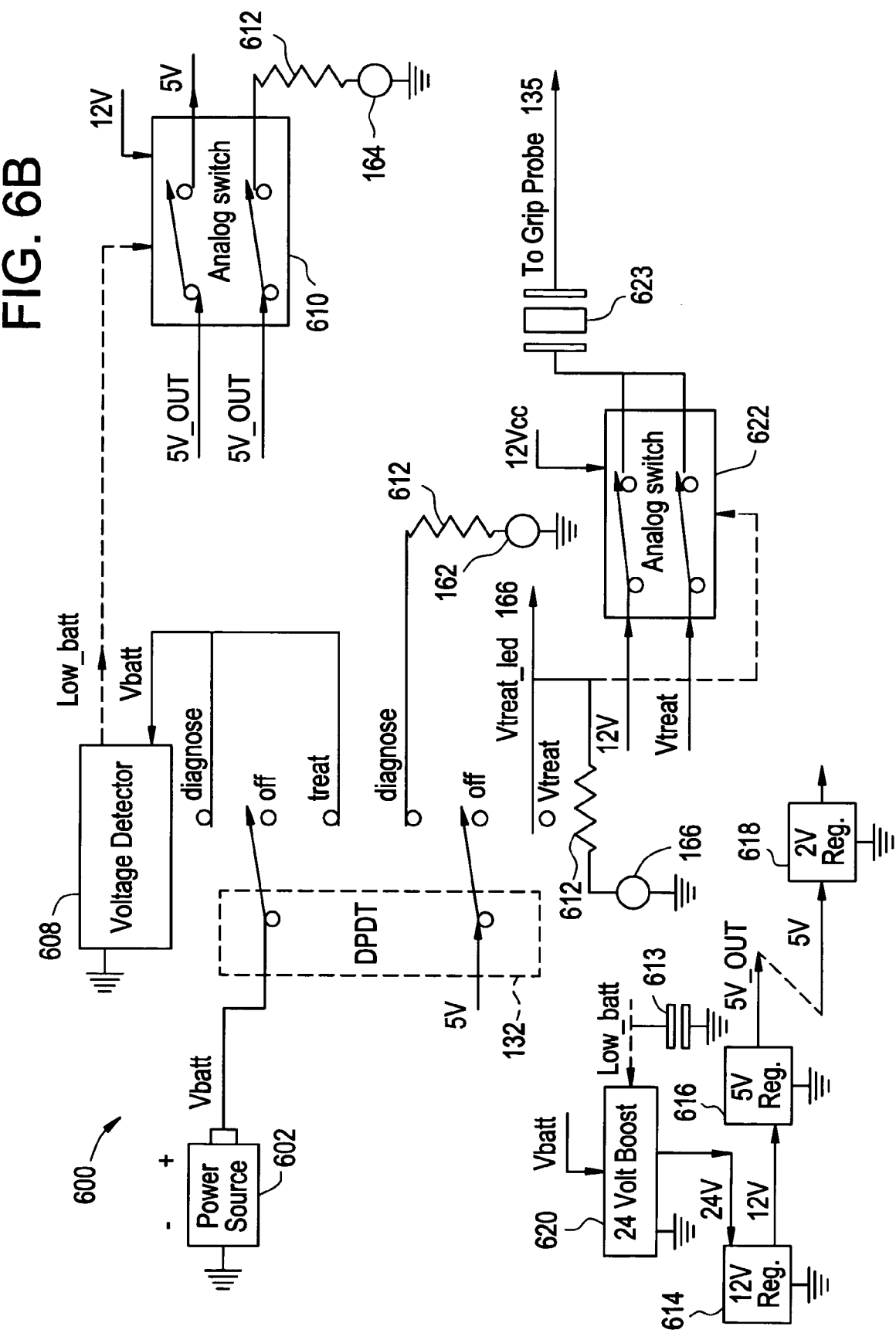
FIG. 6B is a circuit block diagram of part of the main electronic circuit in the hand-held electronic acupuncture device 100 in accordance with an example embodiment of the present invention.
Figure 6C:
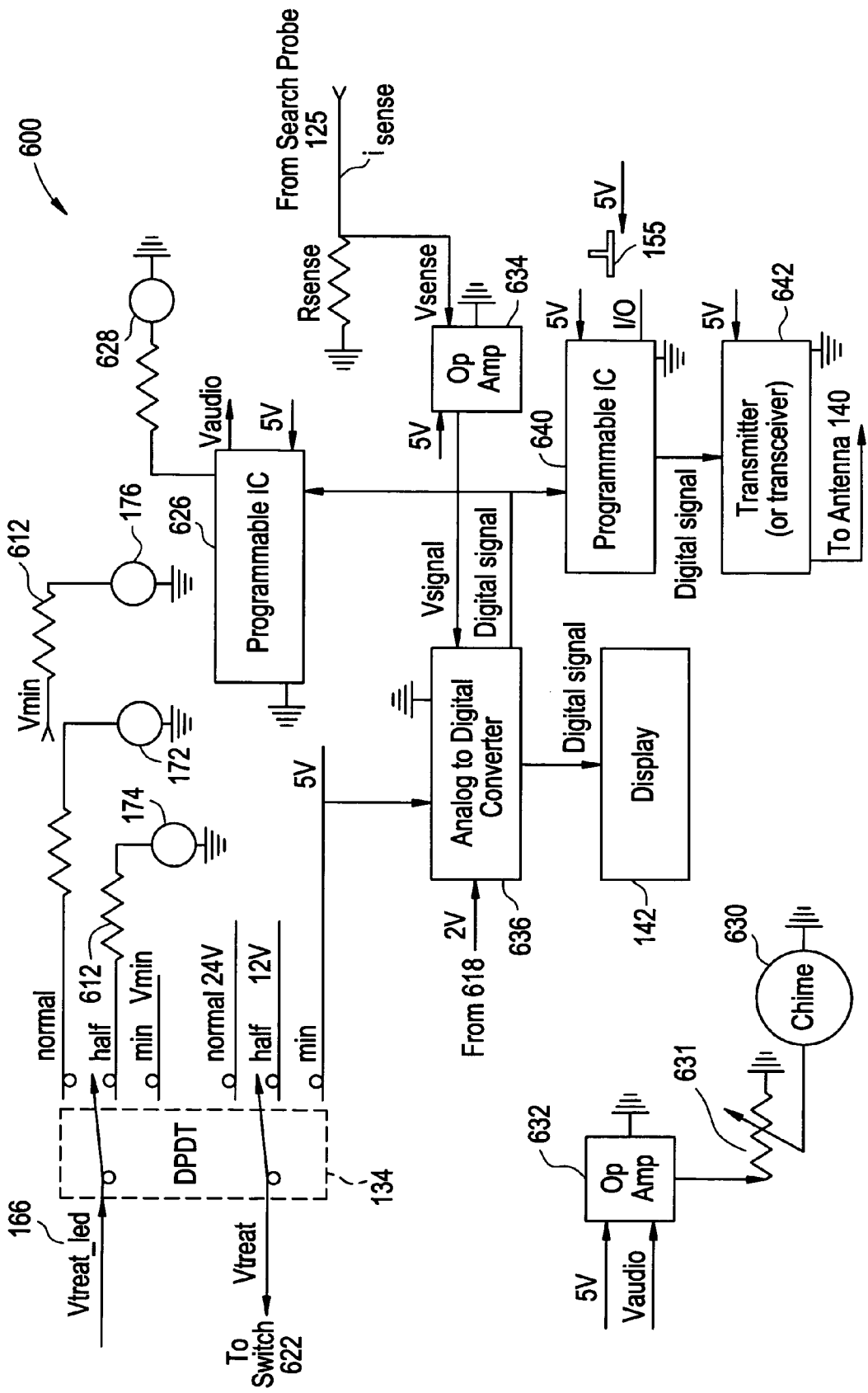
FIG. 6C is a circuit block diagram of part of the main electronic circuit in the hand-held electronic acupuncture device 100 including transmitter circuitry and diagnosis data display/indication circuitry, in accordance with an example embodiment of the present invention.

FIG. 6B is a circuit block diagram of part of a main electronic circuit 600 in the hand-held electronic acupuncture device 100, and FIG. 6C is a circuit block diagram of another part of the main electronic circuit 600 including transmitter circuitry, in accordance with an example embodiment of the present invention.

Referring to FIGS. 6B and 6C, the switch positions diagnose, off and treatment are shown in relation to the power source 602 within the power source compartment 105. Depending on which is selected (as indicated by LEDs 162 or 166, for example), one of a 24 volt, 12 volt or 5/6 volt voltage may be applied. In the diagnosis state or mode, a 12 volt voltage may be applied via regulator 614, high speed analog switch 622 (shut based on the logic signal dotted line from the switch 132) and current limiter 623 to generate a voltage (e.g., $V_{diag}=12V$) through the grip probe 135 and into the patient, to generate a diagnosis current that is measurable ($i_{sense}$) at search probe 125. In the treatment state or mode, actuation of switches 132 and 134 send logic signals (dotted lines) to shut analog switch 622, and to illuminate LED 166 and one of LEDs 172, 174 or 176.

In general, the analog signal received from the patient serves as an input (Vsignal) to ADC 636 for conversion to a suitable digital signal for display on LCD 142. Additionally, the digital signal is formatted by a programmable IC 640 for transmission by transmitter/transreceiver 642 via antenna 140 over air interface 150 (FIG. 1) or other interface (if wired, via wired connection to a USB) to be received, processed/analyzed and/or displayed on the display 220 of the remote computing device 200. As an example, actuation of the record button 155 permits this processing to take place.

High speed analog switches 610 and 624 may be existing off-the-shelf components. Example high speed analog switches usable in main circuit 600 may be those such as the Maxim dual, 5Ω analog switches from Dallas Semiconductor®, part numbers MAX4622 and MAX4623. High speed analog switches 610 and 624 are more robust for low-distortion applications or applications where current switching is required, as compared to mechanical relays. High speed analog switches have generally low power requirements, use less board space and are generally more reliable than mechanical relays, and may be operable from either a single positive supply (i.e., power source 602) or with bipolar supplies, while retaining CMOS-logic input compatibility.

Main circuit 600 may include regulators 614, 616 and 618. Regulator 614 regulates the 24 volt bus voltage output from 24 volt boost circuit 620 down to the 12 volt diagnosis voltage applied to the patient, or to a "half treatment" voltage if switch 134 is selected to half. Regulator 616 may be provided to generate the Vcc for the switches ($5V_{13}$ out) from the 12V output from regulator 614, 5V power for DPDT switch 132, programmable integrated circuits (ICs) 626, 640, op amps 632 and 634 and transmitter 642. Regulator 618 generates a 2V reference voltage for the ADC 636 from the 5V voltage output from regulator 616.

Based on Vbatt and Vdd input thereto, the 24V boost circuit 620 generates a 24V output, which may be input to switch 622 as the normal treatment voltage (Vtreat) used to generate $i_{treat}$ in the patient (when switch 134 set to normal), or which may be regulated by regulator 614 or 616 to a lower treatment voltage (12V (half), 5/6 volts (min)). As shown in FIGS. 6B and 6C, given LEDs 162,164, 166, 172, 174 and 176 are illuminated based on the position of switches 132 and 134. Resistors 612 are provided as voltage dividers for the LEDs.

Main circuit 600 may include a voltage detector 608, which in an example may be a programmable IC. Voltage detector 608 may be programmed to detect a high voltage condition (6VDC— indicating that an incorrect power source is inserted) or a low voltage condition (~3VDC) in the power source 602, so as to take a protective action by sending the appropriate logic signal (see dotted line in FIG. 6B) to shut analog switch 610, energize LED 164 and cutoff 24V boost circuit 620. LED 164 may be illuminated in conjunction with an audible alarm to alert the user of the high/low voltage condition. For example, PIC 626 generates a digital Vaudio signal that is input to op amp 632. The output from op amp 632 is varied by potentiometer 631, so as to produce a variable pitch at chime 630 alerting the user. The low_batt logic signal thus shuts switch 610, cuts out 24V boost circuit 620 and illuminates LED 164. A capacitor 613 is provided in the low_batt input to 24V boost circuit 620. The capacitor 613 acts as a delay, storing charge to allow analog switch 610 to toggle and shut before to low_batt input signal cuts off the 24V boost circuit 620.

Referring to FIG. 6C, the current ($i_{sense}$) received from the patient (via search probe 125) in response to the applied diagnosis or treatment voltage from grip probe 135 is converted into an analog voltage signal Vsense via resistor Rsense, as is known, and input to operational amplifiers 632 and 634 for comparison to the reference voltage so as to generate an amplified signal (Vsignal).

Vsignal is input to programmable IC 626 and ADC 636, which converts the readings to a digital signal that may be displayed as a conductance value on display 142. Programmable IC 626 (and 640) may be off-the-shelf components such as 8/14 pin, 8-bit flash microcontrollers fabricated by Microchip Technology, Inc.®, part number PIC12F509, although other ICs having non-volatile memory may be used, as is evident to one skilled in the art.

As discussed, programmable IC (or PIC) 626 functions to control a point location (visual) indicator LED 628 and the variable frequency chime 630 (audible indicator), based on the value of Vsignal. For example, as the caregiver is moving the search probe around a given meridian energy point as shown in FIG. 5, the display 142 (LCD) will display a rapidly changing current. The PIC 626 illuminates the LED 628 at the highest local current in the vicinity of the measured meridian energy point on the patient's body. The frequency of the chime 630 gradually changes from a lower frequency pitch (via potentiometer 631) to a higher frequency pitch (and vice versa) (as Vsignal increases/decreases due to higher/lower measured instantaneous current) to assist the caregiver in locating the correct meridian point to record data.

Once that point is reached, the user depresses actuation button 155 to temporarily record the data in flash memory. The Vsignal corresponding to the recorded data is also converted at ADC 636 into a digital signal that is displayed at LCD 142 and converted into a suitable format at PIC 640 for transmission as an RF signal (after appropriate modulation and coding at transmitter/transceiver 642) via the antenna 140 to the remote computing device 200 over airlink 150 (or alternatively via a wired interface such as a USB cable, if such is connected between electronic device 100 and remote computing device 200). Although two PICs 626/640 are shown in FIG. 6C, the functions of LED 625, chime 630 and transceiver 642 could be controlled from a single PIC 626 or 640.

Figure 6D:
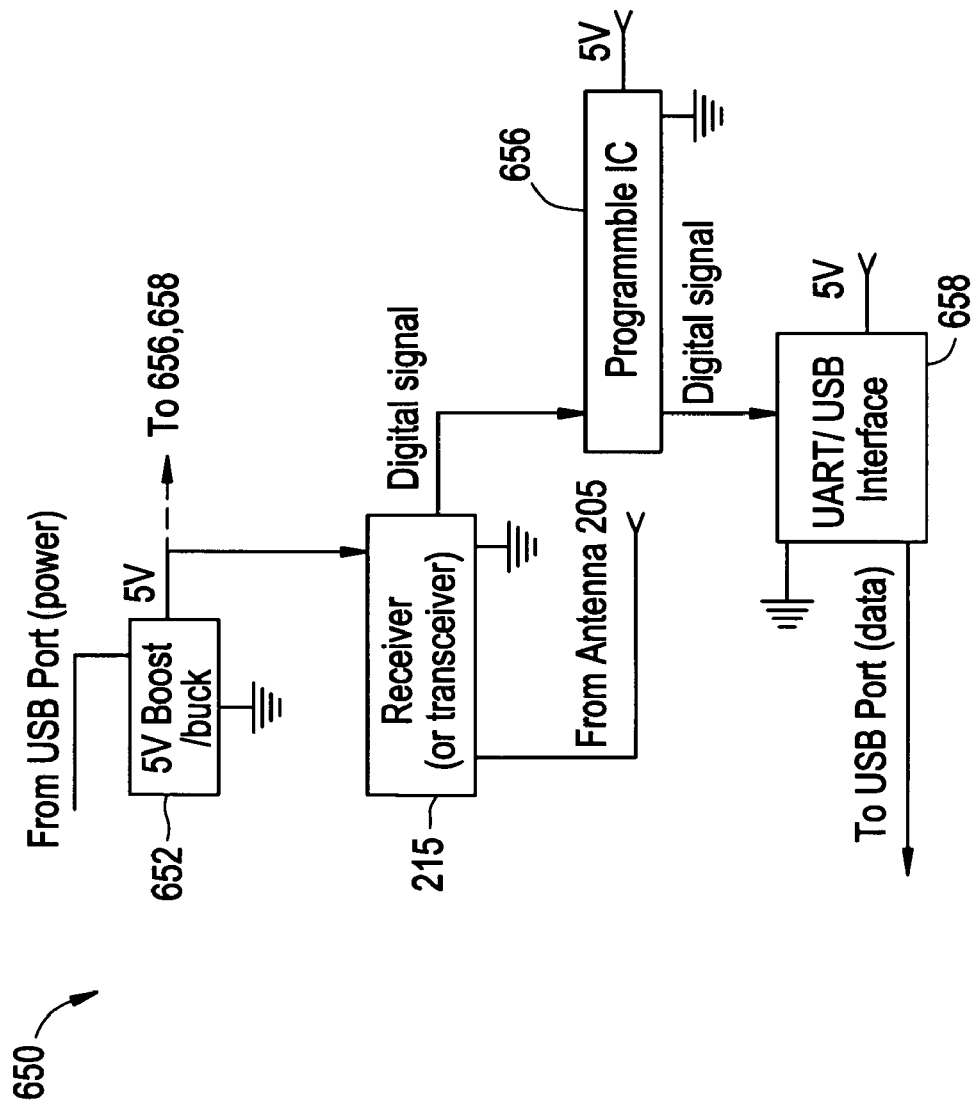
FIG. 6D is a circuit block diagram of part of the receiver circuitry in the remote computing device 200, in accordance with an example embodiment of the present invention.

FIG. 6D is a circuit block diagram of part of the receiver circuitry in the remote computing device 200, in accordance with an example embodiment of the present invention. Receiver circuitry 650 may be powered via a 5V signal from a boost/buck circuit 652 which receives power from a USB port of the remote computing device 200. The 5V signal may be used to power receiver/transceiver 215 (FIG. 1), PIC 656 and UART/USB interface 658.

Transceiver/receiver 215 demodulates and decodes the RF signal received over its antenna into a digital signal that is input to PIC 656. PIC 656 changes the format of the digital signal into a format suitable for the UART/USB interface 658. A Universal Asynchronous Receiver/Transmitter (UART) controller is a computer component that handles asynchronous serial communication. Every computing device contains a UART to manage its serial ports; some internal modems have their own UART. For example, a 16550 UART contains a 16-byte buffer, enabling it to support higher transmission rates than the older 8250 UART.

The UART/USB interface 658 may be an off-the-shelf component such as a CP2102 single-chip USB to UART bridge by Silicon Laboratories®), for example. The UART/USB interface 658 converts data traffic between USB and UART formats so as to separate bytes into individual bits which are transmitted ins sequential fashion to non-networked entities such as processor 210, for example, via a suitable serial data port (USB), for storage in a suitable memory 215, for display on display 220 for analysis by the caregiver, and/or for processing/analysis by processor 210 executing a specified software routine or algorithm, for example.

FIG. 7A illustrates an enlarged view of a main unit assembly of a hand-held electronic acupuncture device in accordance with another example embodiment of the present invention. FIG. 7A is somewhat similar to FIG. 6A, however, the main unit 715 in FIG. 7A is provided with onboard electronics/intelligence, as to be discussed hereafter. Referring to FIG. 7A, main unit 715 may include a display 742 such as an LCD panel (or equivalent display medium), and may be operatively connected to the grip probe 735 and search probe 725. The main unit 715 may include an on/off button 732 (alternatively this may be a switch) and a button/switch 734 for selecting between normal, half and minimum treatment voltages.

Additionally, the main unit 715 may be provided with a multi-function actuation button 750. The multi-function actuation button 750 may include a number of button positions, including stim/sedate 752, a no/skip selection position 754, a yes/next selection position 756, a record position 758 and a show pic (short for "show picture") selection button 759. In an example, multi-function actuation button may be a four-directional, center-push, multifunctional SKRH-series TACT switch. Also as shown in FIG. 7A, LEDs 772, 774 and 776 can be provided for each of the normal, half and minimum treatment voltages. Main unit 715 may include an action LED 764 and treatment and diagnosis LEDs 762, 766.

FIGS. 7B-1 and 7B-2 illustrate a circuit diagram of an electronic circuit included in a hand-held electronic acupuncture device in accordance with another example embodiment of the present invention. As shown in FIGS. 7B-1 and 7B-2, the circuit diagram is of an electronic acupuncture device with intelligence. In this example, the intelligence may be embodied by an integrated semiconductor device such as a microchip 760. The microchip 760 may include a memory unit comprised of RAM and ROM or combinations thereof, a processor (microcontroller) an ADC and an LCD driver, for example. The individual inputs and outputs labeled "A-I" in FIG. 7B-1 are shown between the chip 760 and various other semiconductor devices which may comprise the electronics of the main unit 715. The following Table 1 illustrates certain example functional processing steps and explains the user interaction, result and feedback to user. Table 1 should be read with occasional reference to each of FIG. 7A and FIGS. 7B-1 and 7B-2.

TABLE 1

Functionality Chart corresponding to FIGS. 7A and 7B-1/2

| User Control | What Happens | Feedback to User |
| --- | --- | --- |
| Presses 'On/Off' button 732 | Circuit 700 turns on in Diagnosis mode<br>Clear all RAM/buffers to zeros/defaults<br>Unit 715 places 12 V across probes 725, 735 and holds it during diagnosis mode | LED 762 illuminates beside 'Diagnosis'<br>LCD 742: 'Yes/Next to diagnose'.<br>LCD 742: 'No/Skip for advanced.' |
| Presses 'Yes/Next' 756 | Remains in diagnosis mode | LCD 742: 'Begin diagnosis'<br>LCD 742: Lu9R |
| Presses 'No/Skip' 754 | See 1* below | |
| 1* Presses 'Show Pic' button 759 during diagnosis mode while the unit 715 is displaying the name of a recommended point to be treated (i.e Lu9R) | Unit 715 replaces characters on screen with illustration | LCD 742: illustration of recommended point |
| 5 seconds elapse after 'Show Pic' 759 pressed per conditions above | Unit 715 replaces illustration with data from prior screen | LCD 742: data that was on screen prior to pressing 'Show Pic' button 759 5 seconds ago |
| 3*Places search probe 725 on patient | Current flows from grip probe 735 through patient to search probe 725 | LCD 742: real-time current value |

TABLE 1-continued

Functionality Chart corresponding to FIGS. 7A and 7B-1/2

| User Control | What Happens | Feedback to User |
|---|---|---|
| 5*Presses 'Record' button 758 | Unit 715 measures current in real time<br>Unit 715 stores current reading in buffer<br>Unit 715 displays captured reading | Unit 715 chimes<br>Illuminates 'Action' LED 764<br>LCD 742: buffered value<br>LCD 742: 'reading ok?'<br>LCD 742: 'Yes/Next to save,<br>LCD 742 'No/Skip to discard' |
| Presses 'No/Skip' 754 or lets 20 seconds elapse | Unit 715 clears current reading from buffer | LCD 742: 'reading discarded'<br>LCD 742: 'Yes/Next to retake' |
| Met criteria in step above and then Presses 'Yes/Next' button 756 | Unit 715 reverts back to previous display for point reading | LCD 742: 'data that was on screen prior to pressing 'No/Skip' or letting 20 seconds elapse |
| When presented decision in step 5* above, pressed 'Yes/Next' 756 within 20 sec Presses 'Record' button 758 | Unit 715 shifts current reading from buffer to RAM (temp memory used during operation) | LCD 742: 'reading stored'<br>Unit 715 chimes<br>Illuminates 'Action' LED 764<br>LCD 742: 'Next point'<br>LCD 742: 'next point to be read' |
| Starts over at step 3* above and repeats until all 24 diagnosis points are committed to RAM | Unit 715 stores 24 readings in RAM<br>Unit 715 computes and stores average reading of the 24 readings<br>Unit 715 computes and stores range high and range low values (average reading +/− 20) | LCD 742: 'readings stored'<br>LCD 742: 'Yes/Next to plot'<br>LCD 742: 'No/Skip to skip' |
| Presses 'No/skip' 754 When presented decision of plot or skip, presses 'Yes/Next' 756 | Skip to step 6* below<br>4*Unit 715 presents first 4 stored readings to LCD 742 | LCD 742: 'Lu9L:' value<br>LCD 742: 'Lu9R:' value<br>LCD 742: 'Pc7R:' value<br>LCD 742: 'Pc7L:' value |
| Presses 'Yes/Next' button 756 | Unit 715 cycles thru next 20 points stored in its RAM<br>this will take 5 more screens, total of 6 screens for 24 points at 4 lines per screen | LCD 742: next 20 values |
| Presses 'Yes/Next' button 756 | 6* presents computed data | LCD 742: 'average:' average reading<br>LCD 742: 'hi end:' range high<br>LCD 742 'low end:' range low<br>LCD 742 'Yes/Next to replot' |
| Presses 'Yes/Next' 756<br>1* Presses 'No/Skip' 754<br>Advanced treatment' mode is normal treatment mode w/out recommended points | Back to step 4*above<br>This is the end of Diagnosis mode, beginning of Treatment mode<br>All diagnosis data is lost (unless download from Unit 715 to remote PC 200)<br>Unit 715 removes 12 V from probes 725, 735, sets at no voltage<br>Unit 715 identifies which diagnosis points were above/below range<br>Unit 715 identifies treatment points (pick from 48 points, 1:1 | LED i766 illuminates<br>If average reading = zero/default (i.e. user went straight into treatment), then LCD 742: 'Advanced treatment'<br>Else if all points fell within hi/low range, then LCD 742: 'No treatment required'<br>Else, LCD 742: 'treat:' first treatment point |

TABLE 1-continued

Functionality Chart corresponding to FIGS. 7A and 7B-1/2

| User Control | What Happens | Feedback to User |
|---|---|---|
| | assignment of the 24 for above/below) If at least one reading was above/below range hi/low and average reading >0, Unit 715 presents first recommended treatment point to LCD 742 | |
| Presses 'Show Pic' 759 button during treatment mode while the Unit 715 is displaying the name of a recommended point to be treated (i.e Lu9R) | Unit 715 replaces characters on screen with illustration | LCD 742: illustration of recommended point |
| 5 seconds elapse after 'Show Pic' 759 pressed per conditions above | Unit 715 replaces illustration with data from prior screen | LCD 742: data that was on screen prior to pressing 'Show Pic' button 759 5 seconds ago |
| Presses button 734 (Normal/Half/Min) | Unit 715 cycles from Normal (24 V), Half (12 V), and Min (5 V) as treatment voltages Note—treatment voltage not applied to probes 725/735 until 'Stim/Sedate' button 752 pressed | LED's 772, 774, 776 (normal, half, min) toggle when button 734 pressed. One of these 3 LED's illuminated in Treatment mode. |
| 2* Places search probe 725 on patient Presses 'Stim/Sedate' button 752 | Treatment voltage is placed across probes 725/735 Current flows from grip probe 735 thru patient to search probe 725 Unit 715 measures current (conductance) in real time | LCD 742: real-time current value LCD 742 begins counter, incremented 1 count per second Unit 715 chimes once Illuminates 'Action' LED 764 for entire duration button 752 pressed |
| 7*Releases 'Stim/Sedate' button 752 | Logic opens circuit 700/removes voltage from across probes 725/735 | LCD 742 counter freezes LCD 742: 'Treatment halted' LCD 742: 'Stim/Sedate to continue' LCD 742: 'Yes/Next for next point' |
| Presses 'Stim/Sedate' button 752 | Logic closes circuit places treatment voltage across probes 725/735 | LCD 742 counter re-starts |
| Presses 'Yes/Next' button 756 in response to step 7* above. | Logic places treatment voltage across probes 725/735 | If average reading = zero/default, then LCD 742: 'Advanced treatment' Else if no more recommended treatment points exist, then LCD 742: 'treatment complete' Else, LCD 742: 'treat:' next treatment point |
| Go to 2* above | | |

FIG. 8 is a flow diagram for describing a method of managing meridian energy data of a patient to treat the patient, in accordance with an example embodiment of the present invention. Occasional reference may be made to FIGS. 1, 6A and 7A for the following description.

In general, an example methodology 800 of managing meridian energy data of a patient to treat the patient may include applying (810) a diagnosis voltage to the patient at each of the patient's major energy meridian points. As previously described, power source 602 or 702 may generate a Vbatt which is regulated to an output voltage of 12V applied via grip probe 135/735 into the patient's body. This generates a current through the patient ('diagnosis current'). Data corresponding to the patient's major energy meridian points may be measured (820) based on the applied diagnosis voltage, and stored (830) for analysis.

As discussed, a meridian conductivity value may be determined and stored for each of the patient's major energy meridian points for subsequent analysis and/or display. In an example, manual graphing per the Ryodoraku protocol may be used to determine a prescribed treatment. In another example, a software algorithm may be iterated to automatically prescribe the points to be stimulated or sedated for treatment.

This measured energy meridian point data, as discussed above, is a voltage signal representation of the current from the patient, which is converted into a digital signal representation of the current for storage and/or display, as reflected by a displayed conductance value on a suitable display 142/220, for example.

The measured energy meridian point data of the patient may then be analyzed (840) by the caregiver. In one example, the conductance values may be plotted in each of twelve (12) interior columns by the caregiver using the graph 500 of FIG. 5A to determine the STIM and SED points for treating the patient using the electronic acupuncture device 100. The plot may then be evaluated for determining (850) a relative energy balance across the patient's major energy meridian points. In an example, the recorded conductance data may be displayed (on display 142/220) to facilitate comparison to the graph 500 based on the Ryodoraku protocol.

In another example, a software algorithm executed by the processor 210 of the remote computing device 200 or by the microcontroller in microchip 760 may compare each of the conductance values against the Ryodoraku chart to determine relative energy balance data, e.g., what current (STIM/SED) to apply to each meridian energy point on the patient's body so as to achieve balanced body energy across all meridian points.

Based on the calculated relative energy balance data, a treatment voltage is applied to the patient. (generating a 'treatment' current in the patient) at each of the patient's major energy meridian points to move energy from over-excited meridian points to under-excited meridian points, or vice versa, so as to achieve the desired relative energy balance across the patient's major energy meridian points. As discussed previously, the Vbatt from power source 602/702 may be regulated to output a voltage greater than 12V to be applied to the patient's body, such as in a range of 12 to 24 volts. Additionally, if a patient is overly sensitive to a current generated at 12V or greater, a lower treatment voltage of 5-6 volts may be applied.

Optionally, the methodology may 800 include inputting patient data (805). For example, the patient's pertinent personal data (height, weight, blood type, date of birth, etc.), may be entered, such as through a suitable query window or screen, and cross-checked against a database in remote computing device 200, stored in ROM within main unit 715, or stored in another accessible external memory. This stored patient data may be used by a caregiver for historical trend analysis, to help the caregiver recognize medical conditions that become apparent over time. The caregiver can thus track a patient's progress over repeated treatments, and may permit the gathering and analysis of mass data from multiple patients and caregivers, such as through Internet downloads, to evaluate and improve the efficacy diagnosis or treatment, for example.

Figure 9A:
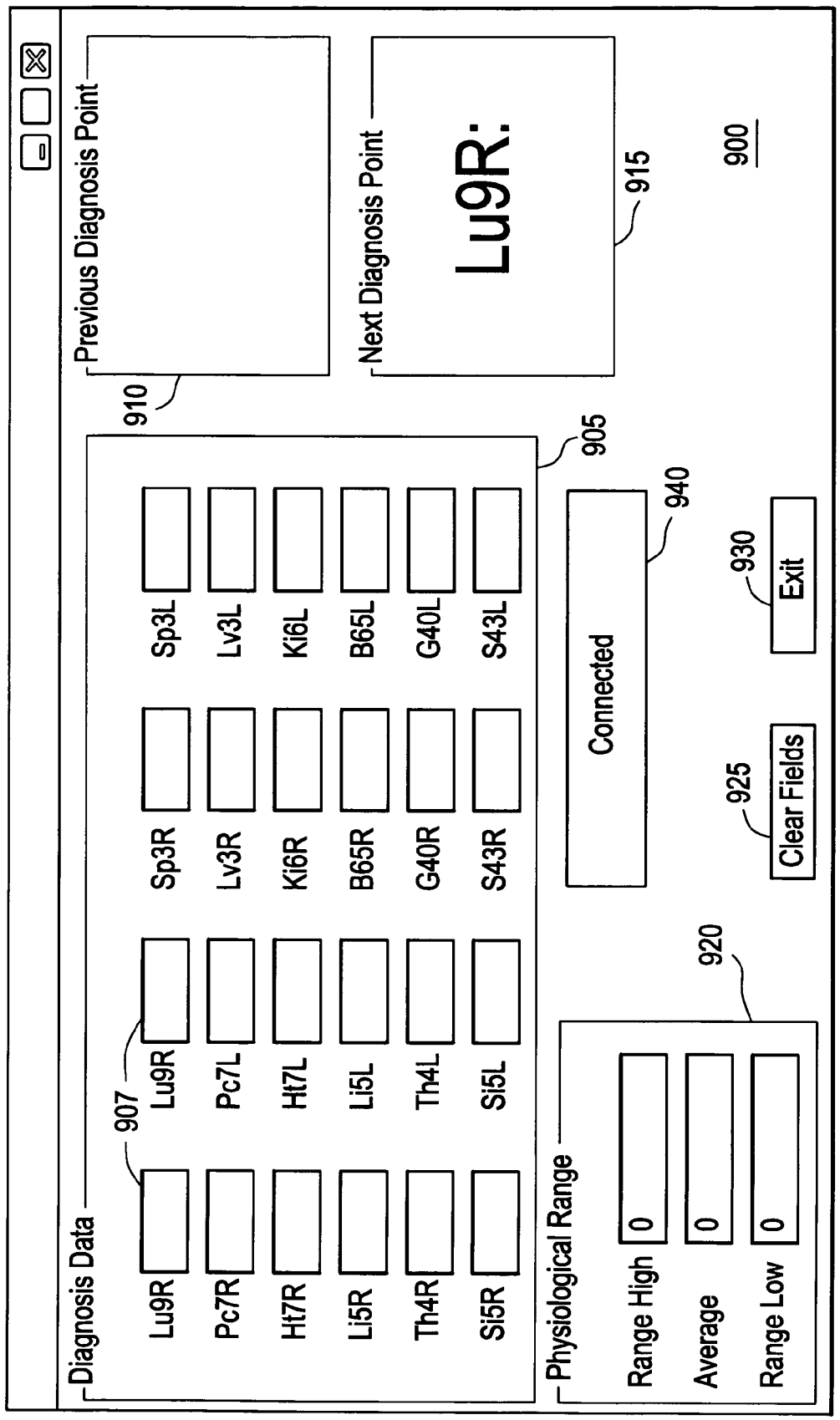

FIGS. 9A and 9B are screen shots illustrating exemplary data displayed to a user of the system 1000 in accordance with an example embodiment of the present invention. Referring to FIG. 9A, example display screen 900 illustrates the recorded data that may be used to analyze a patient for diagnosis and/or treatment. Display screen 900 may include a diagnosis data window 905 which includes data cells 907 for displaying each of the 24 points measured, so as to properly diagnose the patient by running and measuring the 12V diagnosis current through 24 points around the wrist and/or feet of the patient. The 24 points may be evaluated utilizing the Ryodoraku protocol, either by hand or via software implementation.

To assist the caregiver, display screen includes a previous diagnosis point window 910 and a next diagnosis point window 915. These windows shift once the caregiver/patient has pressed the record button 150/758 on the main unit of the electronic acupuncture device. Screen 900 includes a selectable clear fields window 925 and an exit window 930. Screen 900 may optionally include an indicator 940 to inform the caregiver whether communications in system 1000 between the electronic device 100 and remote computing device 200 are connected or disconnected.

FIG. 9B illustrates the display after a complete set of conductance values have been recorded for a patient, as shown in cells 907. As shown in FIG. 9B, screen 900 may further include a psychological range window 920. The Psychological range Window 920 is provided for determining which meridians, if any, are above range (over-excited and in need of sedation) or below range (under-excited and in need of stimulation) and includes a range high cell 922, an average cell 924 and a range low cell 926. The 24 diagnosis readings with physiological ranges may be displayed in graphical format, such as by a colored bar chart, using differing colored bars to show over-excited readings, readings within the physiological range and under-excited readings, for example.

Although described primarily in terms of hardware above, the example methodology implemented by one or more components of the example system described above may also be embodied in software as a computer program. For example, a program in accordance with example embodiments of the present invention may be a computer program product causing a computer or a microprocessor to execute a method of managing meridian energy data of a patient by implementing the functionality as described FIG. 8, for example.

The computer program product may include a computer-readable medium having computer program logic or code portions embodied thereon for enabling a processor of the system in accordance with an example embodiment to perform one or more functions in accordance with the example methodology described above. For example, the computer program logic may cause a processor in one of the remote computing unit 200 (processor 210) or main unit assembly 115/715 of device 100 (e.g., chip 760) to direct the application of the diagnosis voltage to the patient at each of the 12 energy meridian points, and to measure the conductance values based on the current read from the patient through search probe 125/725. The computer program logic may cause the processor to iterate software-based functionality to analyze the measured energy meridian point data and display the data for comparison to a graph based on the Ryodoraku protocol, or to iterate software-based functionality which is configured to compare the data to the Ryodoraku protocol and to determine or calculate a relative energy balance across the patient's major energy meridian points based on the comparison.

The computer-readable storage medium may be a built-in medium installed inside a computer main body such as the remote computing device or a removable medium arranged so that it can be separated from the computer main body and/or so it may be configurable in the main unit of the electronic acupuncture device. Examples of a built-in medium include, but are not limited to, rewriteable non-volatile memories, for example, RAM, ROM, flash memories and hard disks. Examples of a removable medium may include, but are not limited to, optical storage media, for example, CD-ROMs and DVDs; magneto-optical storage media, for example, MOs; magnetism storage media, for example, floppy disks (trademark), cassette tapes, and removable hard disks; media with a built-in rewriteable non-volatile memory, for example, memory cards; and media with a built-in ROM, for example, ROM cassettes.

These programs may also be provided in the form of an externally supplied propagated signal and/or a computer data signal embodied in a carrier wave (e.g., transmission through the internet). The computer data signal embodying one or more instructions or functions of the example methodology as described in FIG. 8 may be carried on a carrier wave for transmission and/or reception by an entity (such as the electronic acupuncture device 100 or remote computing device 200) that executes instructions or functions of the example methodology.

For example, the functions or instructions of the example method may be implemented by processing one or more code segments of the carrier wave in a computer controlling one or more of the components (main unit 115, remote PC 200, etc.) of the example system as shown in any of FIGS. 1, 6A, 6B, 7A or 7B-1/2 where instructions or functions may be executed for implementing one or more functions for managing meridian energy data of a patient. Code segments of the carrier wave in an example may carry instructions to direct the application of the diagnosis current to the patient at each of the 12 energy meridian points and to measure the conductance values based on the current read from the patient through search probe 125. Code segments of the carrier wave may carry instructions to cause a processor to iterate software-based functionality to analyze the measured energy meridian point data and to display the data for comparison to a graph based on the Ryodoraku protocol. In another example, code segments of the carrier wave may carry instructions to a processor for iterating functionality software-based functionality configured to compare the data to the Ryodoraku protocol and to determine or calculate a relative energy balance across the patient's major energy meridian points based on the comparison. Code segments of the carrier wave may further carry instructions to direct the application of the treatment current to the patient to achieve the relative energy balance across the patient's major energy meridian points.

Further, such programs, when recorded on computer-readable storage media, may be readily stored and distributed. The storage medium, as it is read by a computer, may enable the managing of a patient's meridian energy data in accordance with the example methods described herein.

The example embodiments of the present invention having been thus described, it will be obvious that the same may be varied in many ways. For example, the functional blocks of FIGS. 4, 6B-6D, 7B-1/2 and 8 describing the example system, device and/or method may be implemented in hardware, software or a combination thereof. The hardware/software implementations may include a combination of processor(s) and article(s) of manufacture. The article(s) of manufacture may further include storage media and executable computer program(s). The executable computer program(s) may include instructions to perform the described operations or functions. The computer executable program(s) may also be provided as part of externally supplied propagated signal(s).

Such variations are not to be regarded as departure from the spirit and scope of example embodiments of the present invention, and all such modifications as would be obvious to one skilled in the art are intended to be included within the scope of the following claims.

We claim:

1. An electronic acupuncture system for providing noninvasive acupuncture treatment for a patient, comprising:
a hand-held electronic acupuncture device, and
a remote computing device, wherein
the electronic acupuncture device is configured to communicate measurable patient data to the remote computing device for diagnosis or treatment of the patient, and
the electronic device includes a processor configured to apply a variable voltage to the patient and a power source having disposable or rechargeable battery cells and configured to generate a given output voltage under control of the processor that generates a given current in the patient, the rechargeable cells of the power source being rechargeable by way of a recharging stand or cradle of a battery charger providing an AC source of charging current from one of a wall outlet and a computing device, the battery charger configured to upload data stored in the electronic device via the recharging stand or cradle to the remote computing device.

2. The system of claim 1, wherein the remote computing device is configured to store and analyze multiple meridian energy point data contained in the measurable patient data for holistic analysis.

3. The system of claim 1, wherein the remote computing device is configured to store and analyze the measurable patient data for total body diagnosis, and includes a display to indicate multiple points of meridian energy data for a holistic evaluation by one of a caregiver of the patient or the patient.

4. The system of claim 1, wherein the electronic device includes transceiver circuitry for communicating with the remote computing device over an air interface.

5. The system of claim 1, wherein the electronic device is connected to the remote computing device via a communication cable to transmit data to and receive data from the remote computing device.

6. The system of claim 1, wherein the electronic device includes a memory having one or more logic circuits, the memory operatively connected to the processor.

7. The system of claim 1, wherein the electronic device includes a switch actuatable to shift the device between a diagnosis state and a treatment state.

8. The system of claim 7, wherein the electronic device includes a light-emitting diode (LED) indicating the diagnostic state and the treatment state.

9. The system of claim 1, wherein the battery cells are embodied as a plurality of disposable battery cells having an alkaline cell chemistry, or a plurality of rechargeable cells having one of a nickel metal hydride (NiMH), nickel cadmium (NiCd) and lithium-ion (Li-ion) cell chemistry.

10. The system of claim 1, wherein
the electronic device includes a switch actuatable to shift the device between a diagnosis state and a treatment state, and
the power source is configured to output a first constant voltage if the electronic device is in the diagnosis state and a second, different constant voltage if the electronic device is in the treatment state, based on the switch position.

11. The system of claim 1, wherein the electronic device includes an actuation button for control of diagnosis and treatment voltages applied to the patient.

12. The system of claim 11, wherein
the electronic device includes a display and a counter, and
as treatment voltage is flowing into the patient, the display provides a counter indication showing the duration of treatment.

13. The system of claim 12, wherein
the counter automatically rests to zero if electrical connection with the patient is terminated or interrupted, and
the counter is adapted for an incremental increase in count to a given count or an incremental decreasing count to zero.

14. The system of claim 1, further comprising:
a grip probe connected to the electronic device and adapted to be held by a user for applying a voltage to a patient, wherein the user is the patient or a caregiver of the patient.

15. The system of claim 14, wherein the grip probe includes grooved finger-grip surfaces to facilitate grasping of the grip probe by a hand of the user.

16. The system of claim 1, wherein the electronic device includes a pressure sensitive, self-moistening search probe that is adapted to apply pressure against the skin of a patient and to receive a current from the patient.

17. The system of claim 16, wherein
the electronic device includes a display, and
the current from the patient that is received by the search probe is an analog value convertible into a digital signal for display on the electronic device, and/or for processing at the remote computing device.

18. The system of claim 16, wherein
data representative of the current from the patient is communicated to the remote computing device, and
the remote computing device includes a display that is configured to implement a given protocol for graphically displaying a plurality of meridian energy data points corresponding to the received data from the patient on the display.

19. The system of claim 1, wherein the electronic device is configurable to apply one of a given diagnosis voltage and a given, different treatment voltage to the patient.

20. A handheld electronic acupuncture device, comprising:
a handhold area operatively connected to an extension member which includes a main electronics unit, the main unit may including a display thereon and intelligence therein for providing one of diagnosis and/or treatment of a patient based on measurable patient data,
a search probe operatively connected to the main unit, and
a grip probe operatively connected via an electrical connector to the main unit, wherein
the main unit includes a processor configured to apply a variable voltage to the patient and a power source having disposable or rechargeable battery cells and configured to generate a given output voltage under control of the processor that generates a given current in the patient, the rechargeable cells of the power source being rechargeable by way of a recharging stand or cradle of a battery charger providing an AC source of charging current from one of a wall outlet and a computing device, the battery charger configured to upload data stored in the electronic device via the recharging stand or cradle to the remote computing device.

21. The device of claim 20, wherein a patient grasps the grip probe and the search probe is applied to the patient's skin to complete an electrical circuit.

22. The device of claim 20, wherein the power source provides an output voltage to the grip probe into the patient's body, generating a current that is detected at the search probe and processed by the processor for analysis and/or display on the device.

23. The device of claim 20, wherein the grip probe includes grooved finger-grip surfaces to facilitate grasping of the grip probe by the hand of the patient.

24. The device of claim 20, wherein the main unit includes an analog-to-digital converter operatively connected to and/or in communication with the processor to convert an analog voltage representation of measurable current from the patient, received via the search probe, to a suitable digital signal for display on the main unit.

25. The device of claim 20, wherein the display is a liquid crystal display (LCD) driven by an LCD driver operatively connected to and/or in communication with the processor.

26. The device of claim 20, further comprising a memory unit operatively connected to and/or in communication with the processor and including one or more logic circuits.

27. The device of claim 26, wherein the memory unit is composed of read-only memory (ROM) or random access memory (RAM) or combinations thereof.

28. The device of claim 20, wherein the main unit further includes:
a memory unit operatively connected to and/or in communication with the processor,
an analog-to-digital converter (ADC) operatively connected to and/or in communication with the processor, and
a LCD driven by an LCD driver operatively connected to and/or in communication with the processor,
wherein the ADC is configured to convert an analog voltage representation of measurable current from the patient, received via the search probe, to a suitable digital signal for display on the LCD.

29. The device of claim 28, wherein each of the processor, memory unit, ADC and LCD driver are integrated on a single semiconductor device.

30. The device of claim 20, wherein the main unit includes an actuation button thereon configured as a one-button control for diagnosis and treatment of the patient.

31. The device of claim 30, wherein the actuation button is configured to variably control an administration of treatment voltage.

32. The device of claim 31, wherein, as the treatment voltage is flowing into the patient, the display displays a counter indication from a counter showing the duration of treatment.

33. The device of claim 32, wherein
the counter automatically rests to zero if electrical connection with the patient is terminated or interrupted, and
the counter is adapted for an incremental increase in count to a given count or an incremental decreasing count to zero.

34. The device of claim 20, wherein the main unit includes a switch actuatable to shift the device between a diagnosis state and a treatment state.

35. The device of claim 20, wherein
the battery cells of the power source are embodied as disposable alkaline cells, or rechargeable NiMH, NiCd or lithium-ion cells for providing an output voltage current flowing to the grip probe and though the patient's body, to be received as a current value at the search probe and processed by the main unit for analysis and/or display, and
the main unit further includes an on/off switch for providing a source of voltage from the power source.

36. An electronic acupuncture device for providing noninvasive acupuncture treatment for a patient, comprising:
a main electronics unit, and
a search probe operatively attached thereto,
wherein the device is configured to apply a diagnosis voltage to a patient and measure a current from the patient representing energy meridian data of the patient, and to apply a different treatment voltage to the patient based on an analysis of the energy meridian data, and
wherein the main unit includes a processor configured to apply a variable voltage to the patient and a power source having disposable or rechargeable battery cells and configured to generate a given output voltage under control of the processor that generates a given current in the patient, the rechargeable cells of the power source being rechargeable by way of a recharging stand or cradle of a battery charger providing an AC source of charging current from one of a wall outlet and a computing device, the battery charger configured to upload data stored in the electronic device via the recharging stand or cradle to the remote computing device.

37. The device of claim 36, wherein the main unit includes mechanical means facilitating the search probe to maintain consistent pressure against the patients skin to permit the device to record energy meridian data from the patient.

38. The device of claim 36, further comprising a conductive handle attached to the main unit for completing the circuit though the patient for self-administration of treatment or diagnosis voltage.

* * * * *

UNITED STATES PATENT AND TRADEMARK OFFICE
CERTIFICATE OF CORRECTION

PATENT NO. : 7,693,579 B2
APPLICATION NO. : 11/377881
DATED : April 6, 2010
INVENTOR(S) : Hindinger et al.

It is certified that error appears in the above-identified patent and that said Letters Patent is hereby corrected as shown below:

Column 1, lines 31, 41, 67, "Chi" should read --chi--; line 45, "1950's" should read --1950s--

Column 2, line 16, "PC," should read --PC--; line 50, "which" should read --that--; line 55, "unit," should read --unit--

Column 3, line 22, "is another example of a search in accordance with an example embodiment" should read --is another example of a search probe in accordance with an example embodiment--

Column 4, line 16, "such as a Blackberry®, Treo®, or Palm Pilot®, for example" should read --such as a Blackberry®, Treo®, or Palm Pilot®--; line 32, "such as drawing power from its USB port via an adapter fx, for example" should read --such as drawing power from its USB port via and adapter fx--; line 38, "the patient grips the grip probe 135 in their hand" should read --the patient grips the grip probe 135 in his/her hand--

Column 5, line 13, "hardwired" should read --hard-wired--; line 31, "such as any of the Pentium® line of microprocessors by Intel®, for example" should read --such as any of the Pentium® line of microprocessors by Intel®--

Column 6, line 5, "such as the MH-C200™ universal battery charger by MAHA Energy Corp.™, for example" should read --such as the MH-C200™ universal battery charger by MAHA Energy Corp.™--; line 39, "in lieu of a digital microprocessor" is redundant and should be removed; line 55, "which in an example may be double-position" should read --which, in an example, may be double-position--; line 62, "hammer head" should read --hammerhead--; line 66, "which" should read --that--

Signed and Sealed this
Twenty-ninth Day of March, 2011

David J. Kappos
*Director of the United States Patent and Trademark Office*

CERTIFICATE OF CORRECTION (continued)
U.S. Pat. No. 7,693,579 B2

Column 7, line 5, "provides a mechanical boundary of the hammer head tip 262 longitudinal motion" should read --provides a mechanical boundary for the hammerhead tip's 262 longitudinal motion--; line 17, "plunger head 255 longitudinal motion" should read --plunger head's 255 longitudinal motion--; line 32, "hammer head" should read --hammerhead--; line 58, "cut-away" should read --cutaway--; line 59, "two piece" should read --two-piece--; line 61, "be" should read --by--; line 62, "such as a pin, screw, etc." should read --(pin, screw, etc,)--; line 66, "non-conductive" should read --nonconductive--; line 67, "proximate" should read --proximal--

Column 8, line 8, "may permit current" should read --may permit a current--; line 22, "slivers" should read --silvers--; line 28, "their" should read --his/her--; line 31, "may in one example have a variable width means" should read --may, in one example, have a variable width means--; line 42, "construction the grip probe" should read --construction, the grip probe--; line 47, "to electronically connect a grip probe 135" should read --to connect a grip probe 135 electronically--

Column 9, line 29, "left most and right most" should read --leftmost and rightmost--; line 62, "hand-held" should read --handheld--; line 67, "may include swiveling features which provides" should read --may include swiveling features that provide--

Column 10, line 12, "which" should read --that--; line 14, "within a hospital, and/or at other locations around the world, for proper diagnosis" should read --within a hospital and/or at other locations around the world for proper diagnosis--; line 41, "one of display 142/220" should read --one of the displays 142/220--; line 50, "off, treatment and diagnose" should read --off, treatment, and diagnose--; line 51, "Additionally switch 134" should read --Additionally, switch 134--; line 67, "which" should read --that--

Column 11, line 4, "24 volt" should read --24-volt--; line 6, "which" should read --that--; line 10, "hand-held" should read --handheld--; line 19 "24 volt, 12 volt, or 5/6 volt" should read --24-volt, 12-volt, or 5/6-volt--; line 21, "high speed" should read --high-speed--; line 24, "into the patient, to generate" should read --into the patient to generate--; line 47, "High speed" should read --High-speed--; line 54, "24 volt" should read --24-volt--; line 55, "12 volt" should read --12-volt--; line 67, "may regulated by regulators" should read --may be regulated by regulators--

Column 12, line 2, "5/6 volt" should read --5-6-volt--; line 6, "which in an example may be a programmable IC" should read --which, in an example, may be a programmable IC--

Column 13, line 21, "such as a CP2102 single-chip USB to UART bridge by Silicon Laboratories®), for example" should read --such as a CP2102 single-chip USB to UART bridge by Silicon Laboratories®--; line 25, "which" should read --that--; line 33, "hand-held" should read --handheld--

Column 14, line 29, "(microcontroller) an ADC and an LCD driver" should read --(microcontroller), an ADC and an LCD driver--

Column 15, user control column, instruction 3, "Presses" should read --presses--; column 4, "pressed" should read --presses--; What Happens column, "this will take 5 more screens" should read --This will take 5 more screens--;

Column 24, line 31, "to variably control an administration of treatment voltage" should read --to control an administration of treatment voltage variably--; line 38, "the counter automatically rests to zero" should read --the counter automatically resets to zero--

Column 26, column 3, "patients" should read --patient's--